United States Patent
Pilgeram et al.

(10) Patent No.: US 11,006,945 B2
(45) Date of Patent: May 18, 2021

(54) SUTURE ANCHOR AND ASSOCIATED METHODS OF USE

(71) Applicant: Stryker Corporation, Kalamazoo, MI (US)

(72) Inventors: Kyle Craig Pilgeram, San Jose, CA (US); Charles McCartney, Denver, CO (US); Harold D. Sampson, Jr., Lone Tree, CO (US); Ross Callison, Denver, CO (US); Anthony P. Napolitano, Chappaqua, NY (US)

(73) Assignee: Stryker Corporation, Kalamazoo, MI (US)

( * ) Notice: Subject to any disclaimer, the term of this patent is extended or adjusted under 35 U.S.C. 154(b) by 456 days.

(21) Appl. No.: 15/964,206

(22) Filed: Apr. 27, 2018

(65) Prior Publication Data

US 2018/0242966 A1 Aug. 30, 2018

Related U.S. Application Data

(63) Continuation of application No. 14/525,636, filed on Oct. 28, 2014, now Pat. No. 9,986,992.

(51) Int. Cl.
*A61B 17/04* (2006.01)
*A61F 2/08* (2006.01)

(52) U.S. Cl.
CPC ...... *A61B 17/0401* (2013.01); *A61B 17/0485* (2013.01); *A61F 2/0811* (2013.01);
(Continued)

(58) Field of Classification Search
CPC ............ A61B 17/0401; A61B 17/0485; A61B 2017/0409; A61B 2017/0414;
(Continued)

(56) References Cited

U.S. PATENT DOCUMENTS

| 749,624 A | 1/1904 | McCullough |
| 1,308,798 A | 7/1919 | Masland |

(Continued)

FOREIGN PATENT DOCUMENTS

| CA | 2713309 A1 | 2/2011 |
| DE | 3131496 A1 | 2/1983 |

(Continued)

OTHER PUBLICATIONS

Australian Examination Report for Application No. 2013202699 dated Feb. 21, 2014.

(Continued)

*Primary Examiner* — Tan-Uyen T Ho
*Assistant Examiner* — Chima U Igboko
(74) *Attorney, Agent, or Firm* — Lerner, David, Littenberg, Krumholz & Mentlik, LLP

(57) ABSTRACT

A method for securing a sleeve in a bore hole in bone. The method includes disposing at least a portion of a length of filament into the bore hole, and implanting the sleeve into the bore hole such that a first pathway extending through first and second ends of the sleeve opens in a direction toward the opening of the bore hole and in a direction toward the base of the bore hole. The method also includes pulling at least a portion of the length of filament through the first pathway of the sleeve, thereby forming a first loop configuration extending from the first end and at least one free end of the length of filament extending from the second end. Also included is passing the at least one free end through the first loop configuration to create a one-way cinch.

16 Claims, 8 Drawing Sheets

(52) U.S. Cl.
CPC ............ *A61B 2017/0403* (2013.01); *A61B 2017/0409* (2013.01); *A61B 2017/0458* (2013.01); *A61F 2002/0852* (2013.01); *A61F 2002/0888* (2013.01)

(58) Field of Classification Search
CPC .... A61B 2017/0458; A61B 2017/0459; A61B 2017/0462; A61B 2017/0475; A61F 2/0811; A61F 2002/0817; A61F 2002/0823; A61F 2002/0835; A61F 2002/0852; A61F 2002/0858; A61F 2002/0888
See application file for complete search history.

(56) References Cited

U.S. PATENT DOCUMENTS

| | | |
|---|---|---|
| 1,624,530 A | 4/1927 | Caruso |
| 2,073,903 A | 3/1937 | O'Neil |
| 2,250,434 A | 7/1941 | Dugaw |
| 2,267,925 A | 12/1941 | Johnston |
| 2,382,019 A | 8/1945 | Miller |
| 2,461,947 A | 2/1949 | Weber |
| 2,494,229 A | 1/1950 | Collison |
| 2,515,365 A | 7/1950 | Zublin |
| 2,547,571 A | 4/1951 | Ettinger |
| 2,773,672 A | 12/1956 | Holmes et al. |
| 2,808,632 A | 10/1957 | Cline |
| 2,833,284 A | 5/1958 | Springer |
| 3,384,085 A | 5/1968 | Hall |
| 3,407,889 A | 10/1968 | Hjalsten et al. |
| 3,461,875 A | 8/1969 | Hall |
| 3,554,192 A | 1/1971 | Isberner |
| 3,580,256 A | 5/1971 | Wilkinson et al. |
| 3,608,095 A | 9/1971 | Barry |
| 3,659,597 A | 5/1972 | Wolfers |
| 3,750,671 A | 8/1973 | Hedrick |
| 3,810,456 A | 5/1974 | Karman |
| 3,845,772 A | 11/1974 | Smith |
| 3,867,932 A | 2/1975 | Huene |
| 3,892,232 A | 7/1975 | Neufeld |
| 3,976,079 A | 8/1976 | Samuels et al. |
| 3,981,051 A | 9/1976 | Brumlik |
| 4,212,569 A | 7/1980 | Andersson et al. |
| 4,265,231 A | 5/1981 | Scheller, Jr. et al. |
| 4,328,839 A | 5/1982 | Lyons et al. |
| 4,483,562 A | 11/1984 | Schoolman |
| 4,489,446 A | 12/1984 | Reed |
| 4,541,423 A | 9/1985 | Barber |
| 4,594,033 A | 6/1986 | Peetz et al. |
| 4,605,347 A | 8/1986 | Jodock et al. |
| 4,608,972 A | 9/1986 | Small |
| 4,611,515 A | 9/1986 | Marbourg, Jr. |
| 4,635,738 A | 1/1987 | Schillinger et al. |
| 4,646,738 A | 3/1987 | Trott |
| 4,706,659 A | 11/1987 | Matthews et al. |
| 4,728,231 A | 3/1988 | Kunimori et al. |
| 4,741,330 A | 5/1988 | Hayhurst |
| 4,748,872 A | 6/1988 | Brown |
| 4,751,922 A | 6/1988 | DiPietropolo |
| 4,781,182 A | 11/1988 | Purnell et al. |
| 4,823,780 A | 4/1989 | Odensten et al. |
| 4,842,451 A | 6/1989 | Dugger |
| 4,863,471 A | 9/1989 | Mansat |
| 4,872,451 A | 10/1989 | Moore et al. |
| 4,946,462 A | 8/1990 | Watanabe |
| 5,002,546 A | 3/1991 | Romano |
| 5,007,911 A | 4/1991 | Baker |
| 5,021,059 A | 6/1991 | Kensey et al. |
| 5,030,219 A | 7/1991 | Matsen, III et al. |
| 5,037,422 A | 8/1991 | Hayhurst et al. |
| 5,037,423 A | 8/1991 | Kenna |
| 5,061,277 A | 10/1991 | Carpentier et al. |
| 5,064,431 A | 11/1991 | Gilbertson et al. |
| 5,122,134 A | 6/1992 | Borzone et al. |
| 5,123,914 A | 6/1992 | Cope |
| 5,133,720 A | 7/1992 | Greenberg |
| 5,139,520 A | 8/1992 | Rosenberg |
| 5,141,520 A | 8/1992 | Goble et al. |
| 5,163,940 A | 11/1992 | Bourque |
| 5,165,494 A | 11/1992 | Barr |
| 5,186,268 A | 2/1993 | Clegg |
| 5,190,548 A | 3/1993 | Davis |
| 5,203,595 A | 4/1993 | Borzone et al. |
| 5,203,787 A | 4/1993 | Noblitt et al. |
| RE34,293 E | 6/1993 | Goble et al. |
| 5,234,435 A | 8/1993 | Seagrave, Jr. |
| 5,259,846 A | 11/1993 | Granger et al. |
| 5,269,785 A | 12/1993 | Bonutti |
| 5,269,809 A | 12/1993 | Hayhurst et al. |
| 5,273,380 A | 12/1993 | Musacchia |
| 5,300,077 A | 4/1994 | Howell |
| 5,314,429 A | 5/1994 | Goble |
| 5,320,115 A | 6/1994 | Kenna |
| 5,320,626 A | 6/1994 | Schmieding |
| 5,324,308 A | 6/1994 | Pierce |
| 5,330,468 A | 7/1994 | Burkhart |
| 5,342,376 A | 8/1994 | Ruff |
| 5,350,383 A | 9/1994 | Schmieding et al. |
| RE34,762 E | 10/1994 | Goble et al. |
| 5,374,269 A | 12/1994 | Rosenberg |
| 5,385,567 A | 1/1995 | Goble |
| 5,391,170 A | 2/1995 | McGuire et al. |
| 5,391,171 A | 2/1995 | Schmieding |
| RE34,871 E | 3/1995 | McGuire et al. |
| 5,395,188 A | 3/1995 | Bailey et al. |
| 5,403,317 A | 4/1995 | Bonutti |
| 5,403,348 A | 4/1995 | Bonutti |
| 5,405,359 A | 4/1995 | Pierce |
| 5,409,494 A | 4/1995 | Morgan |
| 5,417,691 A | 5/1995 | Hayhurst |
| 5,423,824 A | 6/1995 | Akerfeldt et al. |
| 5,423,860 A | 6/1995 | Lizardi et al. |
| 5,437,630 A | 8/1995 | Daniel et al. |
| 5,437,675 A | 8/1995 | Wilson |
| 5,437,677 A | 8/1995 | Shearer et al. |
| 5,441,502 A | 8/1995 | Bartlett |
| 5,443,482 A | 8/1995 | Stone et al. |
| 5,458,604 A | 10/1995 | Schmieding |
| 5,464,407 A | 11/1995 | McGuire |
| 5,464,425 A | 11/1995 | Skiba |
| 5,464,426 A | 11/1995 | Bonutti |
| 5,466,243 A | 11/1995 | Schmieding et al. |
| 5,472,452 A | 12/1995 | Trott |
| 5,486,197 A | 1/1996 | Le et al. |
| 5,488,761 A | 2/1996 | Leone |
| 5,496,348 A | 3/1996 | Bonutti |
| 5,505,736 A | 4/1996 | Reimels et al. |
| 5,520,693 A | 5/1996 | McGuire et al. |
| 5,520,700 A | 5/1996 | Beyar et al. |
| 5,522,846 A | 6/1996 | Bonutti |
| 5,527,316 A | 6/1996 | Stone et al. |
| 5,527,343 A | 6/1996 | Bonutti |
| 5,529,580 A | 6/1996 | Kusunoki et al. |
| 5,531,759 A | 7/1996 | Kensey et al. |
| 5,534,012 A | 7/1996 | Bonutti |
| 5,540,703 A | 7/1996 | Barker, Jr. et al. |
| 5,545,178 A | 8/1996 | Kensey et al. |
| 5,548,862 A | 8/1996 | Curtis |
| 5,569,269 A | 10/1996 | Hart et al. |
| 5,569,306 A | 10/1996 | Thal |
| 5,570,706 A | 11/1996 | Howell |
| 5,571,111 A | 11/1996 | Aboczky |
| 5,573,542 A | 11/1996 | Stevens |
| 5,575,819 A | 11/1996 | Amis |
| 5,584,617 A | 12/1996 | Houser |
| 5,584,695 A | 12/1996 | Lal Sachdeva et al. |
| 5,584,835 A | 12/1996 | Greenfield |
| 5,601,550 A | 2/1997 | Esser |
| 5,601,557 A | 2/1997 | Hayhurst |
| 5,601,561 A | 2/1997 | Terry et al. |
| 5,618,314 A | 4/1997 | Harwin et al. |
| 5,645,545 A | 7/1997 | Bryant |
| 5,645,589 A | 7/1997 | Li |

(56) References Cited

U.S. PATENT DOCUMENTS

| | | |
|---|---|---|
| 5,647,874 A | 7/1997 | Hayhurst |
| 5,649,963 A | 7/1997 | McDevitt |
| 5,658,289 A | 8/1997 | Boucher et al. |
| 5,658,313 A | 8/1997 | Thal |
| 5,662,658 A | 9/1997 | Wenstrom, Jr. |
| 5,664,914 A | 9/1997 | Taniguchi |
| 5,665,110 A | 9/1997 | Chervitz et al. |
| 5,665,111 A | 9/1997 | Ray et al. |
| 5,665,112 A | 9/1997 | Thal |
| 5,667,509 A | 9/1997 | Westin |
| 5,671,695 A | 9/1997 | Schroeder |
| 5,674,279 A | 10/1997 | Wright et al. |
| 5,681,315 A | 10/1997 | Szabo |
| 5,681,320 A | 10/1997 | McGuire |
| 5,681,352 A | 10/1997 | Clancy, III et al. |
| 5,683,401 A | 11/1997 | Schmieding et al. |
| 5,683,418 A | 11/1997 | Luscombe et al. |
| 5,683,419 A | 11/1997 | Thal |
| 5,690,676 A | 11/1997 | DiPoto et al. |
| 5,690,677 A | 11/1997 | Schmieding et al. |
| 5,695,513 A | 12/1997 | Johnson et al. |
| 5,699,657 A | 12/1997 | Paulson |
| 5,702,397 A | 12/1997 | Goble et al. |
| 5,707,374 A | 1/1998 | Schmidt |
| 5,709,708 A | 1/1998 | Thal |
| 5,713,905 A | 2/1998 | Goble et al. |
| 5,716,397 A | 2/1998 | Myers |
| 5,718,717 A | 2/1998 | Bonutti |
| 5,720,765 A | 2/1998 | Thal |
| 5,725,530 A | 3/1998 | Popken |
| 5,725,541 A | 3/1998 | Anspach, III et al. |
| 5,725,557 A | 3/1998 | Gatturna et al. |
| 5,728,136 A | 3/1998 | Thal |
| 5,732,606 A | 3/1998 | Chiang |
| 5,733,306 A | 3/1998 | Bonutti |
| 5,733,307 A | 3/1998 | Dinsdale |
| 5,749,899 A | 5/1998 | Bardin et al. |
| 5,755,724 A | 5/1998 | Yoon |
| 5,755,731 A | 5/1998 | Grinberg |
| 5,766,221 A | 6/1998 | Benderev et al. |
| 5,782,862 A | 7/1998 | Bonutti |
| 5,782,864 A | 7/1998 | Lizardi |
| 5,782,866 A | 7/1998 | Wenstrom, Jr. |
| 5,788,699 A | 8/1998 | Bobst et al. |
| 5,797,918 A | 8/1998 | McGuire et al. |
| 5,810,825 A | 9/1998 | Huebner |
| 5,814,056 A | 9/1998 | Prosst et al. |
| 5,820,464 A | 10/1998 | Parlato |
| 5,836,953 A | 11/1998 | Yoon |
| 5,851,208 A | 12/1998 | Trott |
| 5,885,294 A | 3/1999 | Pedlick et al. |
| 5,888,034 A | 3/1999 | Greenberg |
| 5,891,168 A | 4/1999 | Thal |
| 5,895,179 A | 4/1999 | Gschwend et al. |
| 5,897,574 A | 4/1999 | Bonutti |
| 5,906,626 A | 5/1999 | Carrillo |
| 5,908,423 A | 6/1999 | Kashuba et al. |
| 5,921,986 A | 7/1999 | Bonutti |
| 5,928,244 A | 7/1999 | Tovey et al. |
| 5,941,139 A | 8/1999 | Vodehnal |
| 5,941,883 A | 8/1999 | Sklar |
| 5,947,659 A | 9/1999 | Mays |
| 5,948,002 A | 9/1999 | Bonutti |
| 5,951,559 A | 9/1999 | Burkhart |
| 5,954,747 A | 9/1999 | Clark |
| 5,968,078 A | 10/1999 | Grotz |
| 5,970,697 A | 10/1999 | Jacobs et al. |
| 5,980,539 A | 11/1999 | Kontos |
| 5,980,558 A | 11/1999 | Wiley |
| 5,980,559 A | 11/1999 | Bonutti |
| 5,989,252 A | 11/1999 | Fumex |
| 5,993,451 A | 11/1999 | Burkhart |
| 5,997,541 A | 12/1999 | Schenk |
| 6,007,566 A | 12/1999 | Wenstrom, Jr. |
| 6,007,567 A | 12/1999 | Bonutti |
| 6,010,515 A | 1/2000 | Swain et al. |
| 6,010,525 A | 1/2000 | Bonutti et al. |
| 6,019,767 A | 2/2000 | Howell |
| 6,024,758 A | 2/2000 | Thal |
| 6,030,406 A | 2/2000 | Davis et al. |
| 6,045,574 A | 4/2000 | Thal |
| 6,053,922 A | 4/2000 | Krause et al. |
| 6,068,642 A | 5/2000 | Johnson et al. |
| 6,077,292 A | 6/2000 | Bonutti |
| 6,083,244 A | 7/2000 | Lubbers et al. |
| 6,083,522 A | 7/2000 | Chu et al. |
| 6,120,511 A | 9/2000 | Chan |
| 6,143,017 A | 11/2000 | Thal |
| 6,146,385 A | 11/2000 | Torrie et al. |
| 6,152,949 A | 11/2000 | Bonutti |
| 6,156,039 A | 12/2000 | Thal |
| 6,156,056 A | 12/2000 | Kearns et al. |
| 6,159,234 A | 12/2000 | Bonutti et al. |
| 6,183,461 B1 | 2/2001 | Matsuura et al. |
| 6,187,011 B1 | 2/2001 | Torrie |
| 6,189,422 B1 | 2/2001 | Stihl |
| 6,210,415 B1 | 4/2001 | Bester |
| 6,224,608 B1 | 5/2001 | Ciccolella et al. |
| 6,245,081 B1 | 6/2001 | Bowman et al. |
| 6,254,604 B1 | 7/2001 | Howell |
| 6,258,093 B1 | 7/2001 | Edwards et al. |
| 6,270,501 B1 | 8/2001 | Freiberg et al. |
| 6,296,659 B1 | 10/2001 | Foerster |
| 6,306,138 B1 | 10/2001 | Clark et al. |
| 6,306,159 B1 | 10/2001 | Schwartz et al. |
| 6,312,438 B1 | 11/2001 | Adams |
| 6,343,482 B1 | 2/2002 | Endo et al. |
| 6,352,538 B2 | 3/2002 | McGuire et al. |
| 6,358,253 B1 | 3/2002 | Torrie et al. |
| 6,364,886 B1 | 4/2002 | Sklar |
| 6,383,188 B2 | 5/2002 | Kuslich et al. |
| 6,416,517 B2 | 7/2002 | Harder et al. |
| 6,419,678 B1 | 7/2002 | Asfora |
| 6,419,684 B1 | 7/2002 | Heisler et al. |
| 6,431,801 B2 | 8/2002 | Vasudeva et al. |
| 6,436,100 B1 | 8/2002 | Berger |
| 6,436,124 B1 | 8/2002 | Anderson et al. |
| 6,440,138 B1 | 8/2002 | Reiley et al. |
| 6,440,141 B1 | 8/2002 | Philippon |
| 6,447,518 B1 | 9/2002 | Krause et al. |
| 6,464,713 B2 | 10/2002 | Bonutti |
| 6,474,425 B1 | 11/2002 | Truax et al. |
| 6,475,230 B1 | 11/2002 | Bonutti et al. |
| 6,478,800 B1 | 11/2002 | Fraser et al. |
| 6,485,504 B1 | 11/2002 | Johnson et al. |
| 6,494,272 B1 | 12/2002 | Eppink et al. |
| 6,500,195 B2 | 12/2002 | Bonutti |
| RE37,963 E | 1/2003 | Thal |
| 6,508,830 B2 | 1/2003 | Steiner |
| 6,511,498 B1 | 1/2003 | Fumex |
| 6,517,578 B2 | 2/2003 | Hein |
| 6,544,281 B2 | 4/2003 | ElAttrache et al. |
| 6,558,386 B2 | 5/2003 | Cragg |
| 6,558,390 B2 | 5/2003 | Cragg |
| 6,569,187 B1 | 5/2003 | Bonutti et al. |
| 6,572,635 B1 | 6/2003 | Bonutti |
| 6,575,979 B1 | 6/2003 | Cragg |
| 6,599,310 B2 | 7/2003 | Leung et al. |
| 6,610,080 B2 | 8/2003 | Morgan |
| 6,635,073 B2 | 10/2003 | Bonutti |
| 6,638,279 B2 | 10/2003 | Bonutti |
| 6,638,283 B2 | 10/2003 | Thal |
| 6,641,597 B2 | 11/2003 | Burkhart et al. |
| 6,660,023 B2 | 12/2003 | McDevitt et al. |
| 6,712,822 B2 | 3/2004 | Re et al. |
| 6,716,234 B2 | 4/2004 | Grafton et al. |
| 6,730,092 B2 | 5/2004 | Songer |
| 6,740,090 B1 | 5/2004 | Cragg et al. |
| 6,746,451 B2 | 6/2004 | Middleton et al. |
| 6,773,450 B2 | 8/2004 | Leung et al. |
| 6,780,188 B2 | 8/2004 | Clark et al. |
| 6,783,533 B2 | 8/2004 | Green et al. |
| 6,790,210 B1 | 9/2004 | Cragg et al. |
| 6,805,697 B1 | 10/2004 | Helm et al. |

(56) References Cited

U.S. PATENT DOCUMENTS

| | | |
|---|---|---|
| 6,824,552 B2 | 11/2004 | Robison et al. |
| 6,830,570 B1 | 12/2004 | Frey et al. |
| 6,848,152 B2 | 2/2005 | Genova et al. |
| 6,863,672 B2 | 3/2005 | Reiley et al. |
| 6,874,978 B2 | 4/2005 | Gongola |
| 6,878,150 B1 | 4/2005 | McGuire et al. |
| 6,887,259 B2 | 5/2005 | Lizardi |
| 6,893,445 B1 | 5/2005 | Revie et al. |
| 6,899,716 B2 | 5/2005 | Cragg |
| 6,921,403 B2 | 7/2005 | Cragg et al. |
| 6,923,811 B1 | 8/2005 | Carl et al. |
| 6,923,814 B1 | 8/2005 | Hildebrand et al. |
| 6,936,052 B2 | 8/2005 | Gellman et al. |
| 6,955,683 B2 | 10/2005 | Bonutti |
| 6,960,214 B2 | 11/2005 | Burkinshaw |
| 6,984,241 B2 | 1/2006 | Lubbers et al. |
| 6,991,636 B2 | 1/2006 | Rose |
| 6,994,719 B2 | 2/2006 | Grafton |
| 6,994,725 B1 | 2/2006 | Goble |
| 6,995,683 B2 | 2/2006 | Smithson et al. |
| 7,008,431 B2 | 3/2006 | Simonson |
| 7,018,144 B2 | 3/2006 | Sasagawa et al. |
| 7,025,770 B2 | 4/2006 | McGuire et al. |
| 7,029,479 B2 | 4/2006 | Tallarida et al. |
| 7,029,490 B2 | 4/2006 | Grafton et al. |
| 7,041,107 B2 | 5/2006 | Pohjonen et al. |
| 7,048,754 B2 | 5/2006 | Martin et al. |
| 7,056,331 B2 | 6/2006 | Kaplan et al. |
| 7,060,073 B2 | 6/2006 | Frey et al. |
| 7,067,132 B2 | 6/2006 | Grabstein et al. |
| 7,077,863 B2 | 7/2006 | Schmieding et al. |
| 7,087,058 B2 | 8/2006 | Cragg |
| 7,087,073 B2 | 8/2006 | Bonutti |
| 7,204,839 B2 | 4/2007 | Dreyfuss et al. |
| 7,217,279 B2 | 5/2007 | Reese |
| 7,217,290 B2 | 5/2007 | Bonutti |
| 7,225,512 B2 | 6/2007 | Genova et al. |
| 7,235,091 B2 | 6/2007 | Thornes |
| 7,241,297 B2 | 7/2007 | Shaolian et al. |
| 7,258,692 B2 | 8/2007 | Thelen et al. |
| 7,261,016 B2 | 8/2007 | Miller |
| 7,285,124 B2 | 10/2007 | Foerster |
| 7,309,338 B2 | 12/2007 | Cragg |
| 7,326,215 B2 | 2/2008 | Myers et al. |
| 7,331,263 B2 | 2/2008 | Erickson et al. |
| 7,371,253 B2 | 5/2008 | Leung et al. |
| 7,381,213 B2 | 6/2008 | Lizardi |
| 7,488,322 B2 | 2/2009 | Brunnett et al. |
| 7,488,329 B2 | 2/2009 | Thelen et al. |
| 7,494,490 B2 | 2/2009 | Justin |
| 7,500,977 B2 | 3/2009 | Assell et al. |
| 7,503,920 B2 | 3/2009 | Siegal |
| 7,520,898 B2 | 4/2009 | Re et al. |
| 7,563,266 B2 | 7/2009 | Camino et al. |
| 7,578,836 B2 | 8/2009 | Justin et al. |
| 7,585,300 B2 | 9/2009 | Cha |
| 7,601,155 B2 | 10/2009 | Petersen |
| 7,601,165 B2 | 10/2009 | Stone |
| 7,604,636 B1 | 10/2009 | Walters et al. |
| 7,608,098 B1 | 10/2009 | Stone et al. |
| 7,611,521 B2 | 11/2009 | Lubbers et al. |
| 7,621,912 B2 | 11/2009 | Harms et al. |
| 7,621,940 B2 | 11/2009 | Harms et al. |
| 7,624,487 B2 | 12/2009 | Trull et al. |
| 7,651,509 B2 | 1/2010 | Bojarski et al. |
| 7,651,515 B2 | 1/2010 | Mack et al. |
| 7,658,751 B2 | 2/2010 | Stone et al. |
| 7,666,189 B2 | 2/2010 | Gerber et al. |
| 7,678,134 B2 | 3/2010 | Schmieding et al. |
| 7,749,250 B2 | 7/2010 | Stone et al. |
| 7,776,049 B1 | 8/2010 | Curran et al. |
| 7,803,173 B2 | 9/2010 | Burkhart et al. |
| 7,857,829 B2 | 12/2010 | Kaplan et al. |
| 7,857,830 B2 | 12/2010 | Stone et al. |
| 7,875,057 B2 | 1/2011 | Cook et al. |
| 7,875,058 B2 | 1/2011 | Holmes, Jr. |
| 7,879,037 B2 | 2/2011 | Brunnett et al. |
| 7,892,235 B2 | 2/2011 | Ellis |
| 7,892,256 B2 | 2/2011 | Grafton et al. |
| 7,901,431 B2 | 3/2011 | Shumas |
| 7,905,903 B2 | 3/2011 | Stone et al. |
| 7,905,904 B2 | 3/2011 | Stone et al. |
| 7,909,547 B2 | 3/2011 | Jordan et al. |
| 7,909,851 B2 | 3/2011 | Stone et al. |
| 7,913,365 B2 | 3/2011 | Genova et al. |
| 7,914,539 B2 | 3/2011 | Stone et al. |
| 7,918,874 B2 | 4/2011 | Siegal |
| 7,959,650 B2 | 6/2011 | Kaiser et al. |
| 7,963,967 B1 | 6/2011 | Woods |
| 7,981,117 B2 | 7/2011 | Newton et al. |
| 7,981,140 B2 | 7/2011 | Burkhart |
| 7,993,369 B2 | 8/2011 | Dreyfuss |
| 7,996,967 B2 | 8/2011 | Genova et al. |
| 7,996,968 B2 | 8/2011 | Genova et al. |
| 8,002,733 B2 | 8/2011 | Kraft et al. |
| 8,011,072 B2 | 9/2011 | Genova et al. |
| 8,015,678 B2 | 9/2011 | Genova et al. |
| 8,020,263 B2 | 9/2011 | Genova et al. |
| 8,028,387 B2 | 10/2011 | Genova et al. |
| 8,028,388 B2 | 10/2011 | Genova et al. |
| 8,032,996 B2 | 10/2011 | Trull et al. |
| 8,043,253 B2 | 10/2011 | Kraft et al. |
| 8,057,500 B2 | 11/2011 | Mitusina |
| 8,070,750 B2 | 12/2011 | Wenstrom, Jr. et al. |
| 8,083,770 B2 | 12/2011 | Ruff et al. |
| 8,088,130 B2 | 1/2012 | Kaiser et al. |
| 8,100,940 B2 | 1/2012 | Leung et al. |
| 8,109,700 B2 | 2/2012 | Jordan et al. |
| 8,114,088 B2 | 2/2012 | Miller |
| 8,118,834 B1 | 2/2012 | Goraltchouk et al. |
| 8,118,836 B2 | 2/2012 | Denham et al. |
| 8,123,750 B2 | 2/2012 | Norton et al. |
| 8,128,640 B2 | 3/2012 | Harris et al. |
| 8,128,658 B2 | 3/2012 | Kaiser et al. |
| 8,128,669 B2 | 3/2012 | Bonutti |
| 8,133,231 B2 | 3/2012 | Martinek et al. |
| 8,137,382 B2 | 3/2012 | Denham et al. |
| 8,147,514 B2 | 4/2012 | Bonutti |
| 8,162,997 B2 | 4/2012 | Struhl |
| 8,172,846 B2 | 5/2012 | Brunnett et al. |
| 8,216,273 B1 | 7/2012 | Goraltchouk et al. |
| 8,231,654 B2 | 7/2012 | Kaiser et al. |
| 8,231,674 B2 | 7/2012 | Albertorio et al. |
| 8,241,305 B2 | 8/2012 | Stone |
| 8,246,652 B2 | 8/2012 | Ruff |
| 8,267,959 B2 | 9/2012 | Fallman |
| 8,273,106 B2 | 9/2012 | Stone et al. |
| 8,292,921 B2 | 10/2012 | Stone et al. |
| 8,298,262 B2 | 10/2012 | Stone et al. |
| 8,303,604 B2 | 11/2012 | Stone et al. |
| 8,312,942 B2 | 11/2012 | Ho et al. |
| 8,317,825 B2 | 11/2012 | Stone |
| 8,337,525 B2 | 12/2012 | Stone et al. |
| 8,343,187 B2 | 1/2013 | Lamson et al. |
| 8,361,113 B2 | 1/2013 | Stone et al. |
| 8,366,713 B2 | 2/2013 | Long et al. |
| 8,394,129 B2 | 3/2013 | Morgenstern Lopez et al. |
| 8,398,678 B2 | 3/2013 | Baker et al. |
| 8,409,253 B2 | 4/2013 | Stone et al. |
| 8,439,976 B2 | 5/2013 | Albertorio et al. |
| 8,460,338 B2 | 6/2013 | Goraltchouk et al. |
| 8,460,379 B2 | 6/2013 | Albertorio et al. |
| 8,469,998 B2 | 6/2013 | Sojka et al. |
| 8,512,340 B2 | 8/2013 | Easley et al. |
| 8,518,087 B2 | 8/2013 | Lopez et al. |
| 8,562,645 B2 | 10/2013 | Stone et al. |
| 8,591,578 B2 | 11/2013 | Albertorio et al. |
| 8,597,333 B2 | 12/2013 | Morgenstern Lopez et al. |
| 8,623,051 B2 | 1/2014 | Bojarski et al. |
| 8,663,324 B2 | 3/2014 | Schmieding et al. |
| 8,801,800 B2 | 8/2014 | Bagga et al. |
| 8,814,905 B2 | 8/2014 | Sengun et al. |
| 8,821,543 B2 | 9/2014 | Hernandez et al. |
| 8,821,544 B2 | 9/2014 | Sengun et al. |

(56) References Cited

U.S. PATENT DOCUMENTS

| | | |
|---|---|---|
| 8,821,545 B2 | 9/2014 | Sengun |
| 9,370,350 B2 | 6/2016 | Norton |
| 9,445,803 B2 | 9/2016 | Marchand et al. |
| 9,451,938 B2 | 9/2016 | Overes et al. |
| 2001/0002436 A1 | 5/2001 | Bowman et al. |
| 2002/0019635 A1 | 2/2002 | Wenstrom et al. |
| 2002/0183758 A1 | 12/2002 | Middleton et al. |
| 2002/0188301 A1 | 12/2002 | Dallara et al. |
| 2003/0032961 A1 | 2/2003 | Pelo et al. |
| 2003/0176919 A1 | 9/2003 | Schmieding |
| 2003/0195565 A1 | 10/2003 | Bonutti |
| 2003/0220646 A1 | 11/2003 | Thelen et al. |
| 2003/0233098 A1 | 12/2003 | Markworth |
| 2004/0010264 A1 | 1/2004 | Acker et al. |
| 2004/0010287 A1 | 1/2004 | Bonutti |
| 2004/0030346 A1 | 2/2004 | Frey et al. |
| 2004/0073227 A1 | 4/2004 | Dreyfuss et al. |
| 2004/0073306 A1 | 4/2004 | Eichhorn et al. |
| 2004/0092933 A1 | 5/2004 | Shaolian et al. |
| 2004/0149093 A1 | 8/2004 | Tang |
| 2004/0193168 A1 | 9/2004 | Long et al. |
| 2004/0193217 A1 | 9/2004 | Lubbers et al. |
| 2004/0208717 A1 | 10/2004 | Greenhalgh |
| 2004/0260300 A1 | 12/2004 | Gorensek et al. |
| 2004/0267277 A1 | 12/2004 | Zannis et al. |
| 2005/0015153 A1 | 1/2005 | Goble et al. |
| 2005/0033362 A1 | 2/2005 | Grafton |
| 2005/0038427 A1 | 2/2005 | Perriello et al. |
| 2005/0070906 A1 | 3/2005 | Clark et al. |
| 2005/0080400 A1 | 4/2005 | Corcoran et al. |
| 2005/0137600 A1 | 6/2005 | Jacobs et al. |
| 2005/0137601 A1 | 6/2005 | Assell et al. |
| 2005/0143741 A1 | 6/2005 | Timmermans et al. |
| 2005/0177168 A1 | 8/2005 | Brunnett et al. |
| 2005/0187537 A1 | 8/2005 | Loeb et al. |
| 2005/0203527 A1 | 9/2005 | Carrison et al. |
| 2005/0228399 A1 | 10/2005 | Kubo et al. |
| 2005/0251159 A1 | 11/2005 | Ewers et al. |
| 2005/0251208 A1 | 11/2005 | Elmer et al. |
| 2005/0261604 A1 | 11/2005 | Stephens et al. |
| 2005/0283156 A1 | 12/2005 | Schmieding et al. |
| 2005/0288710 A1 | 12/2005 | Fallin et al. |
| 2006/0001518 A1 | 1/2006 | Hayashi et al. |
| 2006/0004369 A1 | 1/2006 | Patel et al. |
| 2006/0015108 A1 | 1/2006 | Bonutti |
| 2006/0015110 A1 | 1/2006 | Pepper |
| 2006/0074434 A1 | 4/2006 | Wenstrom et al. |
| 2006/0079904 A1 | 4/2006 | Thal |
| 2006/0100631 A1 | 5/2006 | Sullivan et al. |
| 2006/0155329 A1 | 7/2006 | Grafton et al. |
| 2006/0178748 A1 | 8/2006 | Dinger et al. |
| 2006/0189993 A1 | 8/2006 | Stone |
| 2006/0190042 A1 | 8/2006 | Stone et al. |
| 2006/0212055 A1 | 9/2006 | Karabey et al. |
| 2006/0247641 A1 | 11/2006 | Re et al. |
| 2006/0247642 A1 | 11/2006 | Stone et al. |
| 2006/0282085 A1 | 12/2006 | Stone et al. |
| 2006/0293689 A1 | 12/2006 | Miller et al. |
| 2007/0010843 A1 | 1/2007 | Green |
| 2007/0010857 A1 | 1/2007 | Sugimoto et al. |
| 2007/0032800 A1 | 2/2007 | Ortiz et al. |
| 2007/0093840 A1 | 4/2007 | Pacelli et al. |
| 2007/0185532 A1 | 8/2007 | Stone et al. |
| 2007/0191853 A1 | 8/2007 | Stone |
| 2007/0213734 A1 | 9/2007 | Bleich et al. |
| 2007/0213735 A1 | 9/2007 | Saadat et al. |
| 2007/0225721 A1 | 9/2007 | Thelen et al. |
| 2007/0233151 A1 | 10/2007 | Chudik |
| 2007/0255317 A1 | 11/2007 | Fanton et al. |
| 2007/0260259 A1 | 11/2007 | Fanton et al. |
| 2007/0276392 A1 | 11/2007 | Beyar et al. |
| 2007/0288023 A1 | 12/2007 | Pellegrino et al. |
| 2007/0288031 A1 | 12/2007 | Dreyfuss et al. |
| 2008/0004659 A1 | 1/2008 | Burkhart et al. |
| 2008/0009904 A1 | 1/2008 | Bourque et al. |
| 2008/0027446 A1 | 1/2008 | Stone et al. |
| 2008/0027457 A1 | 1/2008 | Dienst et al. |
| 2008/0046009 A1 | 2/2008 | Albertorio et al. |
| 2008/0058816 A1 | 3/2008 | Philippon et al. |
| 2008/0065080 A1 | 3/2008 | Assell et al. |
| 2008/0065092 A1 | 3/2008 | Assell et al. |
| 2008/0065114 A1 | 3/2008 | Stone et al. |
| 2008/0071282 A1 | 3/2008 | Assell et al. |
| 2008/0082127 A1 | 4/2008 | Stone et al. |
| 2008/0082128 A1 | 4/2008 | Stone |
| 2008/0109037 A1 | 5/2008 | Steiner et al. |
| 2008/0114364 A1 | 5/2008 | Goldin et al. |
| 2008/0114399 A1 | 5/2008 | Bonutti |
| 2008/0132932 A1 | 6/2008 | Hoeppner et al. |
| 2008/0140078 A1 | 6/2008 | Nelson et al. |
| 2008/0140092 A1 | 6/2008 | Stone et al. |
| 2008/0140093 A1 | 6/2008 | Stone et al. |
| 2008/0140116 A1 | 6/2008 | Bonutti |
| 2008/0147063 A1 | 6/2008 | Cauldwell et al. |
| 2008/0147064 A1 | 6/2008 | Cauldwell et al. |
| 2008/0147071 A1 | 6/2008 | Serra et al. |
| 2008/0154275 A1 | 6/2008 | Assell et al. |
| 2008/0161814 A1 | 7/2008 | McAllister et al. |
| 2008/0167660 A1 | 7/2008 | Moreau et al. |
| 2008/0188854 A1 | 8/2008 | Moser |
| 2008/0188935 A1 | 8/2008 | Saylor et al. |
| 2008/0243163 A1 | 10/2008 | Masseglia et al. |
| 2008/0249481 A1 | 10/2008 | Crainich et al. |
| 2008/0255613 A1 | 10/2008 | Kaiser et al. |
| 2008/0262544 A1 | 10/2008 | Burkhart |
| 2008/0275431 A1* | 11/2008 | Stone ................ A61B 17/0401 606/1 |
| 2008/0275453 A1 | 11/2008 | Lafosse et al. |
| 2008/0306483 A1 | 12/2008 | Iannarone |
| 2008/0312689 A1 | 12/2008 | Denham et al. |
| 2008/0319478 A1 | 12/2008 | Foerster et al. |
| 2009/0012526 A1 | 1/2009 | Fletcher |
| 2009/0018654 A1 | 1/2009 | Schmieding et al. |
| 2009/0024130 A1 | 1/2009 | Lombardo |
| 2009/0054928 A1 | 2/2009 | Denham et al. |
| 2009/0062854 A1 | 3/2009 | Kaiser et al. |
| 2009/0076514 A1 | 3/2009 | Haines |
| 2009/0082805 A1 | 3/2009 | Kaiser et al. |
| 2009/0099554 A1 | 4/2009 | Forster et al. |
| 2009/0105775 A1 | 4/2009 | Mitchell et al. |
| 2009/0131940 A1 | 5/2009 | Brunnett et al. |
| 2009/0138015 A1 | 5/2009 | Conner et al. |
| 2009/0138042 A1 | 5/2009 | Thal |
| 2009/0143784 A1 | 6/2009 | Petersen et al. |
| 2009/0149858 A1 | 6/2009 | Fanelli et al. |
| 2009/0157081 A1 | 6/2009 | Homan et al. |
| 2009/0157124 A1 | 6/2009 | Ferragamo et al. |
| 2009/0160112 A1 | 6/2009 | Ostrovsky |
| 2009/0171359 A1 | 7/2009 | Sterrett |
| 2009/0192468 A1 | 7/2009 | Stone |
| 2009/0194446 A1 | 8/2009 | Miller et al. |
| 2009/0198258 A1 | 8/2009 | Workman |
| 2009/0216238 A1 | 8/2009 | Stark |
| 2009/0216243 A1 | 8/2009 | Re |
| 2009/0222013 A1 | 9/2009 | Graf et al. |
| 2009/0234386 A1 | 9/2009 | Dean et al. |
| 2009/0234451 A1 | 9/2009 | Manderson |
| 2009/0240104 A1 | 9/2009 | Ogdahl et al. |
| 2009/0248029 A1 | 10/2009 | Paulos |
| 2009/0265002 A1 | 10/2009 | Re et al. |
| 2009/0306671 A1 | 12/2009 | McCormack et al. |
| 2009/0306711 A1 | 12/2009 | Stone et al. |
| 2009/0312763 A1 | 12/2009 | McCormack et al. |
| 2009/0312776 A1 | 12/2009 | Kaiser et al. |
| 2009/0312792 A1 | 12/2009 | Fallin et al. |
| 2009/0312793 A1 | 12/2009 | Huxel et al. |
| 2009/0318961 A1 | 12/2009 | Stone et al. |
| 2009/0326538 A1 | 12/2009 | Sennett et al. |
| 2010/0049196 A1 | 2/2010 | Re |
| 2010/0049202 A1 | 2/2010 | Re |
| 2010/0049203 A1 | 2/2010 | Re |
| 2010/0057045 A1 | 3/2010 | Albritton, IV et al. |
| 2010/0076440 A1 | 3/2010 | Pamichev et al. |
| 2010/0082033 A1 | 4/2010 | Germain |

(56) References Cited

U.S. PATENT DOCUMENTS

| | | |
|---|---|---|
| 2010/0087857 A1 | 4/2010 | Stone et al. |
| 2010/0121332 A1 | 5/2010 | Crainich et al. |
| 2010/0121333 A1 | 5/2010 | Crainich et al. |
| 2010/0145384 A1 | 6/2010 | Stone et al. |
| 2010/0152739 A1 | 6/2010 | Sidebotham et al. |
| 2010/0160962 A1 | 6/2010 | Dreyfuss et al. |
| 2010/0185238 A1 | 7/2010 | Cauldwell et al. |
| 2010/0185283 A1 | 7/2010 | Baird et al. |
| 2010/0191241 A1 | 7/2010 | McCormack et al. |
| 2010/0211075 A1 | 8/2010 | Stone |
| 2010/0241121 A1 | 9/2010 | Logan et al. |
| 2010/0249786 A1 | 9/2010 | Schmieding et al. |
| 2010/0262146 A1 | 10/2010 | Tulkis |
| 2010/0268275 A1 | 10/2010 | Stone et al. |
| 2010/0292731 A1 | 11/2010 | Gittings et al. |
| 2010/0292732 A1 | 11/2010 | Hirotsuka et al. |
| 2010/0292792 A1 | 11/2010 | Stone et al. |
| 2010/0298878 A1 | 11/2010 | Leung et al. |
| 2010/0298879 A1 | 11/2010 | Leung et al. |
| 2010/0305709 A1 | 12/2010 | Metzger et al. |
| 2010/0318122 A1 | 12/2010 | Leung et al. |
| 2011/0009902 A1 | 1/2011 | Leung et al. |
| 2011/0015674 A1 | 1/2011 | Howard et al. |
| 2011/0015675 A1 | 1/2011 | Howard et al. |
| 2011/0022083 A1 | 1/2011 | DiMatteo et al. |
| 2011/0022084 A1 | 1/2011 | Sengun et al. |
| 2011/0046625 A1 | 2/2011 | Boileau et al. |
| 2011/0054526 A1 | 3/2011 | Stone et al. |
| 2011/0087247 A1 | 4/2011 | Fung et al. |
| 2011/0087280 A1 | 4/2011 | Albertorio |
| 2011/0087284 A1 | 4/2011 | Stone et al. |
| 2011/0093010 A1 | 4/2011 | Genova et al. |
| 2011/0098727 A1 | 4/2011 | Kaiser et al. |
| 2011/0106089 A1 | 5/2011 | Brunnett et al. |
| 2011/0106153 A1 | 5/2011 | Stone et al. |
| 2011/0125189 A1 | 5/2011 | Stoll, Jr. et al. |
| 2011/0152927 A1 | 6/2011 | Deng et al. |
| 2011/0160767 A1 | 6/2011 | Stone et al. |
| 2011/0160768 A1 | 6/2011 | Stone et al. |
| 2011/0184516 A1 | 7/2011 | Baird et al. |
| 2011/0208194 A1 | 8/2011 | Steiner et al. |
| 2011/0208239 A1 | 8/2011 | Stone et al. |
| 2011/0208240 A1 | 8/2011 | Stone et al. |
| 2011/0213416 A1 | 9/2011 | Kaiser |
| 2011/0213417 A1 | 9/2011 | Foerster et al. |
| 2011/0218538 A1 | 9/2011 | Sherman et al. |
| 2011/0218625 A1 | 9/2011 | Berelsman et al. |
| 2011/0224799 A1 | 9/2011 | Stone |
| 2011/0264138 A1 | 10/2011 | Avelar et al. |
| 2011/0264140 A1 | 10/2011 | Lizardi et al. |
| 2011/0264141 A1 | 10/2011 | Denham et al. |
| 2011/0270278 A1 | 11/2011 | Overes et al. |
| 2011/0270293 A1 | 11/2011 | Malla et al. |
| 2011/0270306 A1 | 11/2011 | Denham et al. |
| 2011/0295279 A1 | 12/2011 | Stone et al. |
| 2011/0301708 A1 | 12/2011 | Stone et al. |
| 2011/0319896 A1 | 12/2011 | Papenfuss et al. |
| 2012/0004672 A1 | 1/2012 | Giap et al. |
| 2012/0041485 A1 | 2/2012 | Kaiser et al. |
| 2012/0041486 A1 | 2/2012 | Stone et al. |
| 2012/0046693 A1 | 2/2012 | Denham et al. |
| 2012/0053629 A1 | 3/2012 | Reiser et al. |
| 2012/0053630 A1 | 3/2012 | Denham et al. |
| 2012/0053641 A1 | 3/2012 | Meridew |
| 2012/0059417 A1 | 3/2012 | Norton et al. |
| 2012/0059418 A1 | 3/2012 | Denham et al. |
| 2012/0071976 A1 | 3/2012 | May et al. |
| 2012/0089193 A1 | 4/2012 | Stone et al. |
| 2012/0095470 A1 | 4/2012 | Kaiser et al. |
| 2012/0095556 A1 | 4/2012 | Re et al. |
| 2012/0109142 A1 | 5/2012 | Dayan |
| 2012/0109156 A1 | 5/2012 | Overes et al. |
| 2012/0109194 A1 | 5/2012 | Miller et al. |
| 2012/0116452 A1 | 5/2012 | Stone et al. |
| 2012/0123474 A1 | 5/2012 | Zajac et al. |
| 2012/0150203 A1 | 6/2012 | Brady et al. |
| 2012/0150297 A1 | 6/2012 | Denham et al. |
| 2012/0150301 A1 | 6/2012 | Gamache et al. |
| 2012/0165866 A1 | 6/2012 | Kaiser et al. |
| 2012/0165867 A1 | 6/2012 | Denham et al. |
| 2012/0165938 A1 | 6/2012 | Denham et al. |
| 2012/0172986 A1 | 7/2012 | Stone et al. |
| 2012/0179254 A1 | 7/2012 | Saliman |
| 2012/0180291 A1 | 7/2012 | Oren et al. |
| 2012/0197271 A1 | 8/2012 | Astorino et al. |
| 2012/0203231 A1 | 8/2012 | Long et al. |
| 2012/0203288 A1 | 8/2012 | Lange et al. |
| 2012/0209325 A1 | 8/2012 | Gagliano et al. |
| 2012/0239085 A1 | 9/2012 | Schlotterback et al. |
| 2012/0239086 A1 | 9/2012 | Reznik et al. |
| 2012/0245585 A1 | 9/2012 | Kaiser et al. |
| 2012/0253355 A1 | 10/2012 | Murray et al. |
| 2012/0265205 A1 | 10/2012 | Steiner et al. |
| 2012/0290002 A1 | 11/2012 | Astorino |
| 2012/0290004 A1 | 11/2012 | Lombardo et al. |
| 2012/0290006 A1 | 11/2012 | Collins et al. |
| 2012/0296345 A1 | 11/2012 | Wack et al. |
| 2012/0296427 A1 | 11/2012 | Conner et al. |
| 2012/0303046 A1 | 11/2012 | Stone et al. |
| 2013/0012962 A1 | 1/2013 | Stone |
| 2013/0018416 A1 | 1/2013 | Lombardo et al. |
| 2013/0023928 A1 | 1/2013 | Dreyfuss |
| 2013/0023929 A1 | 1/2013 | Sullivan et al. |
| 2013/0023930 A1 | 1/2013 | Stone et al. |
| 2013/0035698 A1 | 2/2013 | Stone et al. |
| 2013/0046341 A1 | 2/2013 | Stone et al. |
| 2013/0053897 A1 | 2/2013 | Brown et al. |
| 2013/0072989 A1 | 3/2013 | Overes et al. |
| 2013/0085568 A1 | 4/2013 | Smith et al. |
| 2013/0096611 A1 | 4/2013 | Sullivan |
| 2013/0096612 A1 | 4/2013 | Zajac et al. |
| 2013/0110165 A1 | 5/2013 | Burkhart et al. |
| 2013/0116730 A1 | 5/2013 | Denham et al. |
| 2013/0131722 A1 | 5/2013 | Marchand et al. |
| 2013/0158601 A1 | 6/2013 | Stone et al. |
| 2013/0165972 A1 | 6/2013 | Sullivan |
| 2013/0178898 A1 | 7/2013 | Arnett et al. |
| 2013/0190818 A1 | 7/2013 | Norton |
| 2013/0190819 A1 | 7/2013 | Norton |
| 2013/0237997 A1 | 9/2013 | Arai et al. |
| 2013/0238025 A1 | 9/2013 | Howard et al. |
| 2013/0245700 A1 | 9/2013 | Choinski |
| 2013/0268000 A1 | 10/2013 | Harner et al. |
| 2013/0296931 A1 | 11/2013 | Sengun |
| 2013/0317544 A1 | 11/2013 | Ferguson et al. |
| 2013/0325063 A1 | 12/2013 | Norton et al. |
| 2013/0345749 A1 | 12/2013 | Sullivan et al. |
| 2014/0039503 A1 | 2/2014 | Pilgeram |
| 2014/0081322 A1 | 3/2014 | Sengun et al. |
| 2014/0135835 A1 | 5/2014 | Stone et al. |
| 2014/0163679 A1 | 6/2014 | Re et al. |
| 2014/0188163 A1 | 7/2014 | Sengun |
| 2014/0257382 A1 | 9/2014 | McCartney |
| 2014/0364906 A1* | 12/2014 | Palese ............... A61B 17/0401 606/232 |

FOREIGN PATENT DOCUMENTS

| | | |
|---|---|---|
| DE | 8903079 U1 | 5/1989 |
| DE | 4231101 A1 | 3/1994 |
| DE | 4243715 A1 | 7/1994 |
| DE | 19503504 A1 | 3/1996 |
| EP | 153831 A2 | 9/1985 |
| EP | 253526 A1 | 1/1988 |
| EP | 0440371 A1 | 8/1991 |
| EP | 0611551 A1 | 8/1994 |
| EP | 1155776 A2 | 11/2001 |
| EP | 1174584 A2 | 1/2002 |
| EP | 1369089 A2 | 12/2003 |
| EP | 1398455 A2 | 3/2004 |
| EP | 2277457 A1 | 1/2011 |
| EP | 2286742 A1 | 2/2011 |
| EP | 2544607 A1 | 1/2013 |
| EP | 2548519 A2 | 1/2013 |

(56) References Cited

FOREIGN PATENT DOCUMENTS

| | | | |
|---|---|---|---|
| EP | 2596755 | A2 | 5/2013 |
| EP | 2662030 | A1 | 11/2013 |
| EP | 2662032 | A1 | 11/2013 |
| FR | 1166884 | A | 11/1958 |
| FR | 2606996 | A1 | 5/1988 |
| FR | 2676638 | A1 | 11/1992 |
| GB | 2093353 | A | 9/1982 |
| WO | 9511631 | A1 | 5/1995 |
| WO | 9628100 | A1 | 9/1996 |
| WO | 9704908 | A1 | 2/1997 |
| WO | 9722301 | A1 | 6/1997 |
| WO | 0024327 | A2 | 5/2000 |
| WO | 0044291 | A1 | 8/2000 |
| WO | 0128457 | A1 | 4/2001 |
| WO | 0160268 | A1 | 8/2001 |
| WO | 03007861 | A1 | 1/2003 |
| WO | 03086221 | A1 | 10/2003 |
| WO | 2004092531 | A2 | 10/2004 |
| WO | 2007/010389 | A1 | 1/2007 |
| WO | 2008128075 | A1 | 10/2008 |
| WO | 2009105880 | A1 | 9/2009 |
| WO | 2011112371 | A1 | 9/2011 |
| WO | 2012134999 | A1 | 10/2012 |
| WO | 2012158583 | A1 | 11/2012 |
| WO | 2013006820 | A1 | 1/2013 |

OTHER PUBLICATIONS

BIOMET Sports Medicine: Micromax Flex Suture Anchor, (2008).
Boccaccini, et al., "Composite Surgical Sutures with Bioactive Glass Coating", J Biomed Mater Res Part B: Appl Biomater 67B, pp. 618-626, 2003.
Bretcanu, et al., "Bioactivity of degradable polymer sutures coated with bioactive glass", Journal of Materials Science: Materials in Medicine, vol. 15, 2004, pp. 893-899.
Burkinshaw, U.S. Appl. No. 60/418,545, filed Oct. 15, 2002.
Charles McCartney, U.S. Appl. No. 13/792,982, filed Mar. 11, 2013, titled "Filamentary Fixation Device and Assembly and Method of Assembly, Manufacture and Use".
Chen et al., European Cells and Materials, vol. 16, Supp. 4, p. 7, 2008.
Chen et al., Journal of Orthopaedic Research, pp. 1432-1438, Nov. 2009.
Chen et al., Poster No. 538, 54th Annual Meeting of the Orthopaedic Research Society, San Francisco, CA Mar. 2008.
Cole et al., American Journal of Sports Medicine, vol. XX, No. X, Apr. 2011, 10 pages.
Conmed: Linvatec: Shoulder Restoration System Y-Knot 1.3mm All Suture Anchor, © 2011 Linvatec Corporation, a subsidiary of ConMed Corporation—CBR 3057 (4 pages).
European Search Report, EP 10173568, dated Nov. 30, 2010.
Extended European Search Report for Application No. EP 12164104 dated Jul. 11, 2012.
Extended European Search Report for Application No. EP14157129 dated Oct. 9, 2014.
Extended European Search Report for Application No. EP14157877 dated Jul. 4, 2016.
Extended European Search Report for Application No. EP14159656 dated Jun. 6, 2014.
HHS Tube, Fort Wayne Metals Research Products Corp., 2009, 2 pages.
Insall et al., The Journal of Bone and Joint Surgery, vol. 49B, No. 2, pp. 211-228, May 1967.
International Search Report and Written Opinion for Application No. PCT/US2012/024303 dated May 24, 2012.
International Search Report and Written Opinion for Application No. PCT/US2014/021231 dated Jun. 25, 2014.
International Search Report PCT/US2010/042264, dated Sep. 30, 2010.
Long et al., U.S. Appl. No. 13/368,730, filed Feb. 8, 2012, titled "Flexible Microdrilling Instrumentation, Kits and Methods".
Marchand et al., U.S. Appl. No. 13/303,849, filed Nov. 23, 2011, titled "Filamentary Suture Anchor".
Medtronic, The VISAO High-Speed Otologic Drill Catalog, 2007, 12 pages.
Partial European Search Report for Application No. EP14151822 dated May 16, 2014.
Partial European Search Report for Appln No. EP12193507 dated Jun. 30, 2017.
Perthes, German Surgery Periodical, vol. 85, Commermorative Publication, pp. 2-18, 1906.
Perthes, Über Operationen bel habitueller Schulterluxaton, Deutsch Zeitschrift für Chirurgie, vol. 85, 1906, pp. 199-227 (English translation provided.).
Pilgeram, Kyle Craig, U.S. Appl. No. 13/588,586, filed Aug. 17, 2012, titled "Soft Tissue Fixation Devices and Methods".
Pilgeram, Kyle Craig, U.S. Appl. No. 13/588,592, filed Aug. 17, 2012, titled "Surgical Instruments and Methods of Use".
Pilgeram, Kyle Craig, U.S. Appl. No. 13/783,804, filed Mar. 4, 2013, titled "Knotless Filamentary Fixation Devices, Assemblies and Systems and Methods of Assembly and Use".
Pilgeram, Kyle Craig, U.S. Appl. No. 61/679,336, filed Aug. 3, 2012, titled "Soft Tissue Fixation Device and Methods".
Stamboulis, et al., "Mechanical properties of biodegradable polymer sutures coated with bioactive glass", Journal of Materials Science: Materials in Medicine, vol. 13, 2002, pp. 843-848.
Steiner et al., U.S. Appl. No. 13/085,882, filed Apr. 13, 2011, titled "Flexible ACL Instrumentation, Kit and Method".
Sugaya et al., Journal of Bone and Joint Surgery, vol. 85-A, No. 5, pp. 878-884, May 2003.
U.S. Appl. No. 12/682,324, filed Sep. 7, 2010.
U.S. Appl. No. 13/070,692, filed Mar. 24, 2011.
U.S. Appl. No. 13/182,851, filed Jul. 14, 2011.
U.S. Appl. No. 13/799,773, filed Mar. 13, 2013.

* cited by examiner

SUTURE ANCHOR AND ASSOCIATED METHODS OF USE

CROSS-REFERENCE TO RELATED APPLICATIONS

This application is a continuation of U.S. application Ser. No. 14/525,636, filed on Oct. 28, 2014, the disclosure of which is incorporated by reference.

BACKGROUND OF THE INVENTION

Soft tissue structures, such as fibrocartilage, ligaments and tendons, facilitate connections between multiple anatomic components. Injuries can partially and/or completely sever such structures leading to immobility and/or dysfunction of the anatomic components. In one example, a shoulder injury may tear a portion of the rotator cuff from its connection to bone, leading to instability of the shoulder joint and causing the naturally tensioned tendon to slacken. In another example, a shoulder injury may separate a portion of the glenoid labrum from the underlying bony structure leading to joint instability.

In some instances surgery may be needed to repair or replace the damaged soft tissue, which often involves anchoring the tissue in its natural position until fully healed. Traditionally, this was achieved by tethering the damaged tissue with a filament to a metal or hardened polymer anchoring device fixed to a bony structure. However, in many instances, such traditional anchoring devices tend to be large in diameter, and must include sufficient material, or other additional structures, to withstand pullout forces. The size of such devices may limit implantation locations in the body, as sufficient bone mass is required to accommodate the device.

Recent trends in tissue anchoring have seen the emergence of "soft" devices, also referred to as "filamentary" fixation devices, in which the anchoring device itself may be constructed of filamentary material, such as suture or the like. Despite the many benefits these filamentary fixation devices provide, such devices, to date, cannot be used to perform knotless surgical procedures, that is, surgical procedures using filaments (such as sutures or the like) where the filament is secured without the need of tying knots, such as half hitches or the like. Further, such devices, while generally capable of being anchored in a smaller bone hole than traditional anchoring devices, may still require a hole too large for certain applications.

BRIEF SUMMARY OF THE INVENTION

Generally, the present disclosure relates to devices, systems, methods and kits for knotless tissue anchoring applications, and in particular, to knotless tissue anchoring applications utilizing a device anchored within a minimal bone hole.

In one aspect of the present disclosure, a method for securing a sleeve in a bore hole in bone, the bore hole having an opening, a base and a wall extending between the base and opening. The method includes disposing at least a portion of a length of filament into the bore hole, and implanting the sleeve into the bore hole such that a first pathway extending through first and second ends of the sleeve opens in a direction toward the opening of the bore hole and in a direction toward the base of the bore hole. The method also includes pulling at least a portion of the length of filament through the first pathway of the sleeve, thereby forming a first loop configuration extending from the first end and at least one free end of the length of filament extending from the second end. Further included in the method is passing the at least one free end through the first loop configuration to create a one-way cinch.

In addition, the length of filament may be adapted to apply tension to a tissue in working relationship with the length of filament. The sleeve may be made of filamentary material. Further, the sleeve may include a sidewall and a plurality of fenestrations extending through the sidewall into the first pathway. When the sleeve is implanted in the bore hole, each of the plurality of fenestrations may be disposed adjacent to and open towards the wall of the bore hole.

Further, the method may also include engaging the length of filament with an inserter device prior to the disposing step, and disengaging the inserter device from the length of filament after the pulling step. The inserter device may include a filament engagement element for engaging and retaining the length of filament, and disengaging the inserter device from the first loop configuration may include moving the filament engagement element from a first position to a second position to release the single length of filament.

Continuing with this aspect, the method may include tensioning the at least one free end such that the first loop configuration, with the at least one free end positioned therethrough, travels toward and into the first pathway of the sleeve. Further, the method may include, prior to the pulling step, pulling the at least one free end and the at least a portion of the length of filament into and through a second pathway in the sleeve from the first end of the sleeve, and maneuvering the at least one free end and the at least a portion of the length of filament around a boundary separating the first and second pathways. The boundary may be a tab formed from a portion of the sleeve. Also, the first and second pathways may intersect at at least one location along the length of the sleeve.

In another aspect of the present disclosure, a method for securing a sleeve in a bore hole in bone, the bore hole having a base, an opening, and a wall disposed between the base and opening. The method includes implanting the sleeve into the bore hole. The sleeve has a length defined between a first end and a second end and a first pathway extending along the length of the sleeve. The method also includes passing at least a portion of a length of filament through the first pathway from the second end through the first end such that the at least a portion of the length of filament forms a first loop configuration that extends from the first pathway at the first end and at least one free segment of the length of filament having a free end that extends from the second end. Additionally, the method includes passing the free end of the at least one free segment through the first loop configuration such that the first loop configuration, with the free end positioned therethrough, forms a one-way cinch.

In addition, the first loop configuration and the first end of the sleeve may trap the at least first free segment to form the one-way cinch. The method may also include, prior to the passing steps, engaging the at least a portion of the length of filament with an inserter device. Further, the method may include disengaging the inserter device from the length of filament after the step of passing the at least a portion of the length of filament through the first pathway to form the first loop configuration. Disengaging the inserter device from the first loop configuration may include actuating a filament engagement element to release the length of filament.

Continuing with this aspect, the sleeve may include an outer surface and a plurality of openings extending from the outer surface into the first pathway. When the sleeve is implanted in the bore hole, each of the plurality of openings may be disposed adjacent to and open towards the wall of the bore hole. The sleeve may also include a second pathway juxtaposed with the first pathway. Prior to passing the at least a portion of the length of filament through the first pathway, the method may include passing the free end and the at least a portion of the length of filament through the second pathway from the first end of the sleeve through the second end of the sleeve. The first and second pathways may intersect at at least one location along the length of the sleeve. The sleeve may be made of filamentary material.

In a further aspect of the present disclosure, a method for securing a sleeve in a bore hole in bone, the bore hole having a base, an opening, and a wall disposed between the base and opening. The method includes implanting the sleeve into the bore hole such that a first end of the sleeve is disposed adjacent the opening of the bore hole and a second end of the sleeve is disposed adjacent the base of the bore hole, such that in this position the sleeve stands in a vertical configuration within the bore hole. The method may also include passing a portion of filament into and along a first pathway of the sleeve, maneuvering the portion of filament around a boundary between the first pathway and a second pathway of the sleeve, forming a first loop configuration extending from the first end of the sleeve, passing the portion of filament through the first loop configuration forming a second loop configuration, and tensioning the portion of filament such that the first loop configuration is pulled towards the first end of the sleeve.

In yet another aspect of the present disclosure, a method for securing a sleeve in a bore hole in bone, the bore hole having a base, an opening, and a wall disposed between the base and opening. The method includes implanting a sleeve into the bore hole such that a first end of the sleeve is disposed adjacent the opening of the bore hole and a second end of the sleeve is disposed adjacent the base of the bore hole, such that in this position the sleeve stands in a vertical configuration within the bore hole. The method also includes passing a portion of filament into and through a first pathway of the sleeve such that the portion of filament forms a first loop configuration extending from the first pathway in a first direction and at least one filament free segment extends from the first pathway in a second direction. The at least one filament free segment has a free end. The method further includes passing the at least one free end of the length of filament through the first loop configuration, and tensioning the at least one free end such that the first loop configuration is pulled toward the first end of the sleeve and the first loop configuration and sleeve traps the at least one filament free segment.

BRIEF DESCRIPTION OF THE DRAWINGS

These and other features, aspects, and advantages of the present invention will become better understood with regard to the following description, appended claims, and accompanying drawings where:

DETAILED DESCRIPTION

Figure 1A:
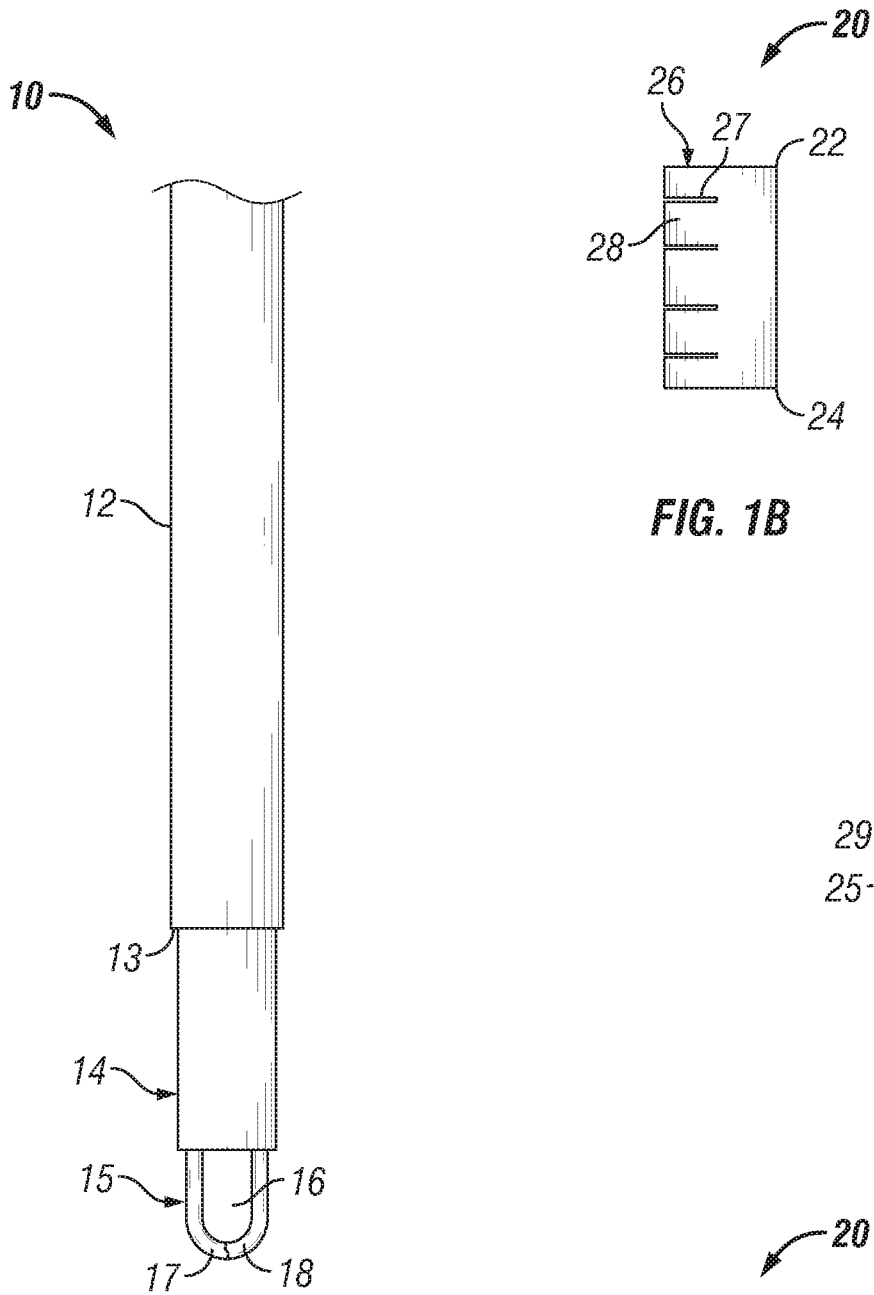
FIG. 1A illustrates one embodiment of an inserter device.

The anchoring devices, assemblies, systems, and associated methods of use of the present invention are intended for use in the repair, reattachment, replacement or otherwise securement of tissue, including both hard tissue (i.e., bone or the like) and soft tissue. Soft tissue may be, for example, meniscus, cartilage, capsule, ligaments and tendons, replacement grafts of any of these soft tissues, or the like. While many of the exemplary methods disclosed herein are directed towards the use of fixation assemblies and systems involving an anchoring sleeve for implantation into a bone hole, other uses, some of which are described herein, are also envisioned. Additionally, the devices, assemblies, systems and methods disclosed herein are contemplated for use in both open surgery and arthroscopic surgery.

As used herein, "proximal" or "proximally" means closer to or towards an operator, e.g., surgeon, while "distal" or "distally" means further from or away from the operator. Also, as used herein, the terms "about," "generally" and "substantially" are intended to mean that slight deviations from absolute are included within the scope of the term so modified.

As used herein, the term "filament" or "filamentary" is defined as a suture or other thread-like material. Such filaments may be constructed of synthetic material (e.g., PLGA, UHMWPE (ultra high molecular weight polyethylene), polyester, PEEK, Nylon, polypropylene, aramids (for example Kevlar®-based fibers) or the like, or blends thereof), organic material (silk, animal tendon, or the like or blends thereof), or blends of both one or more organic materials and one or more synthetic materials. Alternatively, filaments may include thin metal wires. While any of these materials may be used, it is preferable, and is disclosed herein, that the various filaments or filamentary aspects of the present invention be constructed out of suture, such as UHMWPE, polyester or blends thereof.

The present invention relates to the use of suture anchors to secure such filaments in the anatomy, commonly a bore hole formed in bone. As used herein, "suture anchor" can be any structure suitable for securing a filament to bone. In one embodiment, the suture anchor is an anchoring sleeve or sleeve, and preferably, the anchoring sleeve or sleeve is formed of a filamentary material.

FIGS. 1A-1D depict one embodiment of an anchoring sleeve 20 and an inserter device 10 for inserting sleeve 20 into a bore hole in bone. Sleeve 20 may be made from filamentary material and is generally cylindrical in shape and includes a longitudinal axis defined between a first end 22 and second end 24. The sleeve 20 has an aperture 26 extending through the length of sleeve 20 from the first end 22 to the second end 24, forming a pathway therethrough, and several slits 27 formed in a sidewall 25 of the sleeve 20 in a direction transverse to the longitudinal axis. A pair of slits 27 forms a tab 28 out of the sidewall, which is moveable from a position of alignment with the remainder of the sidewall into a position located within aperture 26. When a tab 28 is positioned within the aperture 26, a fenestration 29 is formed in the sidewall 25 of sleeve 20. Sleeve 20 can have a pair of slits 27 forming one tab 28, or multiple pairs of slits 27 forming two or more tabs 28, and, therefore, two or more fenestrations 29, respectively.

Figure 1B:
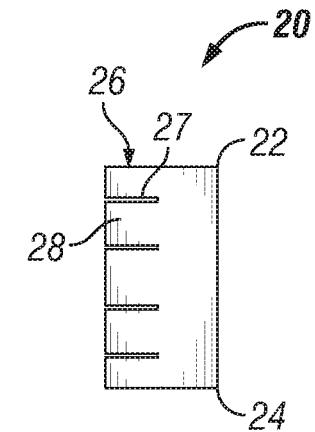
FIG. 1B illustrates one embodiment of an anchoring sleeve in a first condition.

The respective lengths of a pair of slits 27 helps determine the length of each corresponding tab 28, which in turn helps determine how far within the aperture 26 each tab can be located from its initial position aligned with the sidewall, as shown in FIG. 1B. For example, as illustrated, the length of each slit 27 within a pair may be substantially half of the circumference of sleeve 20. In such a configuration, a tab 28 formed by such slits 27 is capable of being pushed into or otherwise positioned into the aperture 26 so that the entire inner surface of the tab 28 can be placed into contact or flush with the entire inner surface of sleeve 20 that is disposed opposite the inner surface of tab 28 (best shown in FIG. 1C). Moreover, in such embodiment, the inner surface of the tab 28 forms an arc having a radius substantially the same as the inner radius of sleeve 20 such that the aperture 26 remains free of obstacles. In an alternative, the tabs 28 may simply be cut and excised from the sleeve, if desired.

Figure 1C:
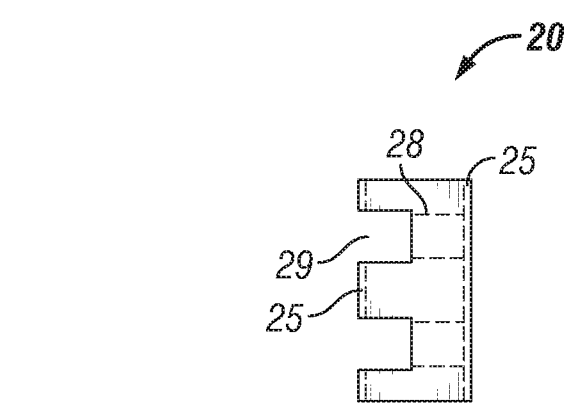
FIG. 1C illustrates the anchoring sleeve of FIG. 1B in a second condition.
Figure 1D:
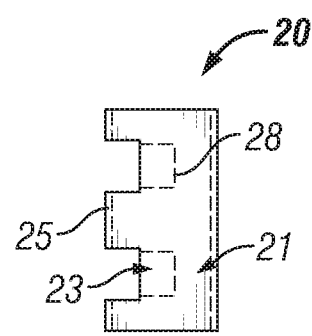
FIG. 1D illustrates the anchoring sleeve of FIG. 1B in an alternative second condition.

The aperture 26 may form a single pathway or be segmented into multiple pathways. As used herein, the term pathway means a route of travel that is defined by a boundary, such as the sleeve sidewall 25 and/or a tab 28 for an item or object, such as a filament, to pass into and/or through the aperture 26. In the embodiment described above in which respective slits 27 have a length substantially half of the circumference of sleeve 20, the aperture 26 may form a single pathway where the tab 28 is either aligned with the sidewall (FIG. 1B) or where the inner surface of the tab 28 fully contacts the inner surface of sleeve 20 opposite the tab 28 (FIG. 1C). In one example where this tab 28 is not pushed or otherwise positioned within the aperture 26 to its full extent, the tab 28 may separate the aperture 26 into a first pathway 21 and a second pathway 23, as best shown in FIG. 1D. In another example, the sidewall 25 itself may provide a boundary separating the aperture 26 into multiple pathways, where, for instance, the sidewall 25 includes fenestrations 29. In such an example, the sidewall 25 between adjacent fenestrations 28 can be inverted and positioned, similar to tab 28, within the aperture 26 to form a boundary separating the aperture 26 into multiple pathways.

In other embodiments, the respective lengths of a pair of slits 27 may be less than half of the circumference of the sleeve 20. In such an embodiment, when a tab 28 formed by such slits 27 is moved to its full extent into the aperture 26, the inner surface of the tab 28 forms an arc having a radius less than the inner radius of sleeve 20. As such, at least a portion of the tab 28 is disposed within the space formed by sleeve 20 without contacting the inner surface of sleeve 20 opposite the inner surface of tab 28, which separates the aperture into at least two pathways (also depicted by FIG. 1D). While it is possible that the respective lengths of a pair of slits 27 can be greater than half of the circumference of the sleeve 20, such lengths are preferably substantially half the length of the circumference or less.

In other embodiments, the sleeve 20 may not have any tabs 28, but rather may have at least one fenestration 29 formed in the sidewall 25. An exemplary anchoring sleeve of this type is the Iconix® line of filamentary fixation products (Stryker Corporation, Kalamazoo, Mich.). Other configurations are also envisioned, examples of which are disclosed in U.S. application Ser. No. 13/783,804, filed Mar. 4, 2013; Ser. No. 13/303,849, filed Nov. 23, 2011; Ser. No. 13/588,586, filed Aug. 17, 2012; Ser. No. 13/588,592, filed Aug. 17, 2012; and U.S. Pat. Nos. 5,989,252 and 6,511,498, the entireties of which are incorporated by reference herein as if fully set forth herein and all of which are assigned to the same entity as the present invention. In these embodiments, the aperture 26 of the sleeve 20 may form a single pathway. However, the sidewall 25 itself may provide a boundary separating the aperture into multiple pathways, where, for instance, the sidewall includes multiple fenestrations 29. In such an example, the fenestrations allow a portion of the sidewall disposed between each fenestration to depress inwardly to form a boundary separating the aperture 26 into multiple pathways.

The inserter 10 generally includes an outer sheath 12 and inner member 14. The outer sheath 12 may be cylindrical and cannulated so that the inner member 14, which may also be cylindrical, is slidingly received within the outer sheath 12. As such, the outer diameter of the outer sheath 12 is larger than the outer diameter of the inner member 14, which forms a shoulder 13 between the outer sheath 12 and inner member 14. The thickness of a sidewall of the outer sheath 12 may be substantially the same thickness as that of the sidewall 25 of the sleeve 20 such that when sleeve 20 is loaded onto inner member 14, the outer surfaces of sleeve 20 are substantially tangent to the outer surfaces of outer sheath 12.

In some embodiments, the inner member 14 may have a groove extending along its length that is complementary to a tongue extending along the length of the inner surface of the outer sheath 12. Such a tongue and groove interface (not shown) can facilitate longitudinal translation of the inner member 14 relative to the outer sheath 12, while prohibiting relative rotational movement. In other embodiments, longitudinal translation and rotational restraint may be provided by a pin and slot interface. In further embodiments, a spring may bias against the inner member 14 extending from a distal end of the outer sheath 12, which may help prevent incidental relative translational movement between the inner member 14 and outer sheath 14 and also provide operator feedback during use.

The inner member 14 includes an actuating member 15 extending from a distal end. As illustrated in FIGS. 1A and 2-4, the actuating member 15 may be a pair of moveable arms 17, 18 that are moveable from a first position to a second position. In the first position, the arms 17, 18, which may be curved, may clamp together at a distal end of each arm. The curvature of the arms 17, 18 forms an opening 16 between the arms to allow for the passage and containment of a filament, such as a suture (as in FIG. 2, for example). In the second position, as in FIG. 4 for example, the distal end of each arm 17, 18 may be separated by a gap so as to allow a filament disposed within the opening 16 to be released without having to unthread the filament from opening 16. Such actuation may be performed by an operator at the proximal end of the inserter device 10, such as by a lever mechanism (not shown) or the like, which may be particularly useful during an arthroscopic procedure, particularly where both ends of the filament are being used, are connected to other objects, or the like. Of course, if a surgical procedure allows one end of the filament to remain free, the arms 17, 18 need not be actuatable.

Figure 2:
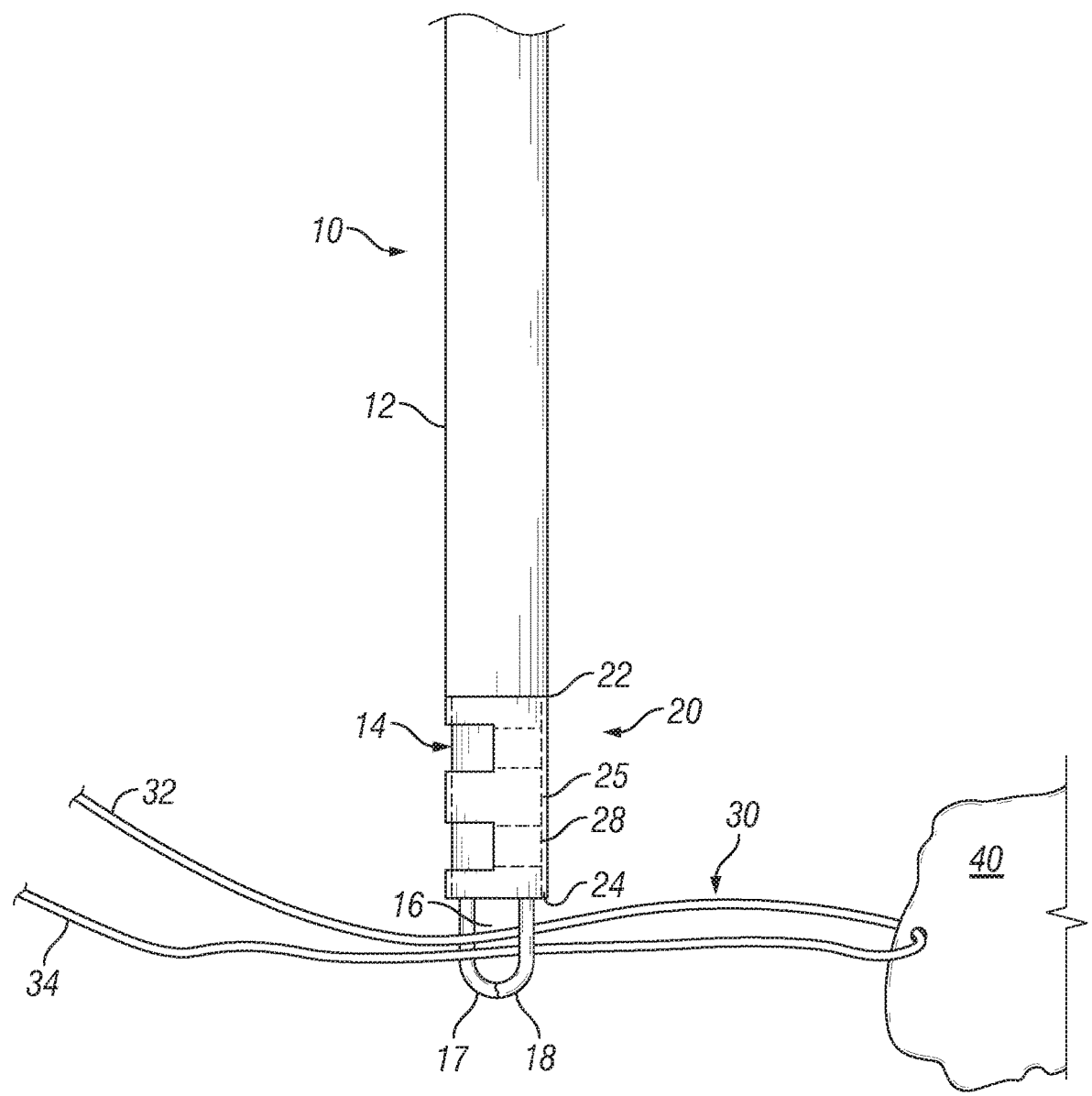
FIG. 2 illustrates a step of one embodiment of a method of use of the inserter and anchoring sleeve of FIGS. 1A and 1B or a method of assembly of an anchoring assembly.

FIGS. 2-7 depict one embodiment of a method of use of inserter 10 and sleeve 20, or, alternatively, a method of assembly of an anchoring assembly comprising a working filament 30 and anchoring sleeve 20. Referring to FIG. 2, sleeve 20 may be loaded onto the inserter 10. This may be done during the manufacturing process and delivered to the operating room in a preloaded configuration, or, alternatively, sleeve 20 may be loaded onto inserter 10 in the operating room during or just prior to the procedure. Generally, sleeve 20 is loaded onto inserter 10 by pushing or otherwise placing the tabs 28 into the aperture 26, preferably to their full extent, and then sliding the sleeve 20 over the inner member 14 such that inner member 14 is disposed within aperture 26 or pathway. In some embodiments, the tabs 28 may remain in their initial position aligned with the sidewall 25 as sleeve 20 is slid over the inner member 14. The first end 22 of sleeve 20 preferably contacts the shoulder 13.

Continuing with the discussion of the illustrated embodiment of a method of securing an anchoring sleeve, and filament, in a bore hole, as in FIG. 2, a working filament 30 may be passed through or around a target tissue 40, which may result in first and second free ends 32, 34 of the working filament 30 extending from the target tissue 40, or only a single free end depending on the technique utilized for ensnaring tissue 40, as is known in the art. Where two free ends 32, 24 result from the ensnarement of tissue 40, the free ends may be passed into the opening 16 between arms 17 and 18 either by threading the free ends 32, 34 through the opening 16 or by grabbing the free ends 32, 34 by actuating the arms 17, 18 from the second to the first position. This may be performed either in vivo or external to the patient. Of course, in certain instances, the filament need not be passed through the tissue prior to being positioned through the opening, though in practice, positioning the filament through tissue first would be standard.

Figure 3:
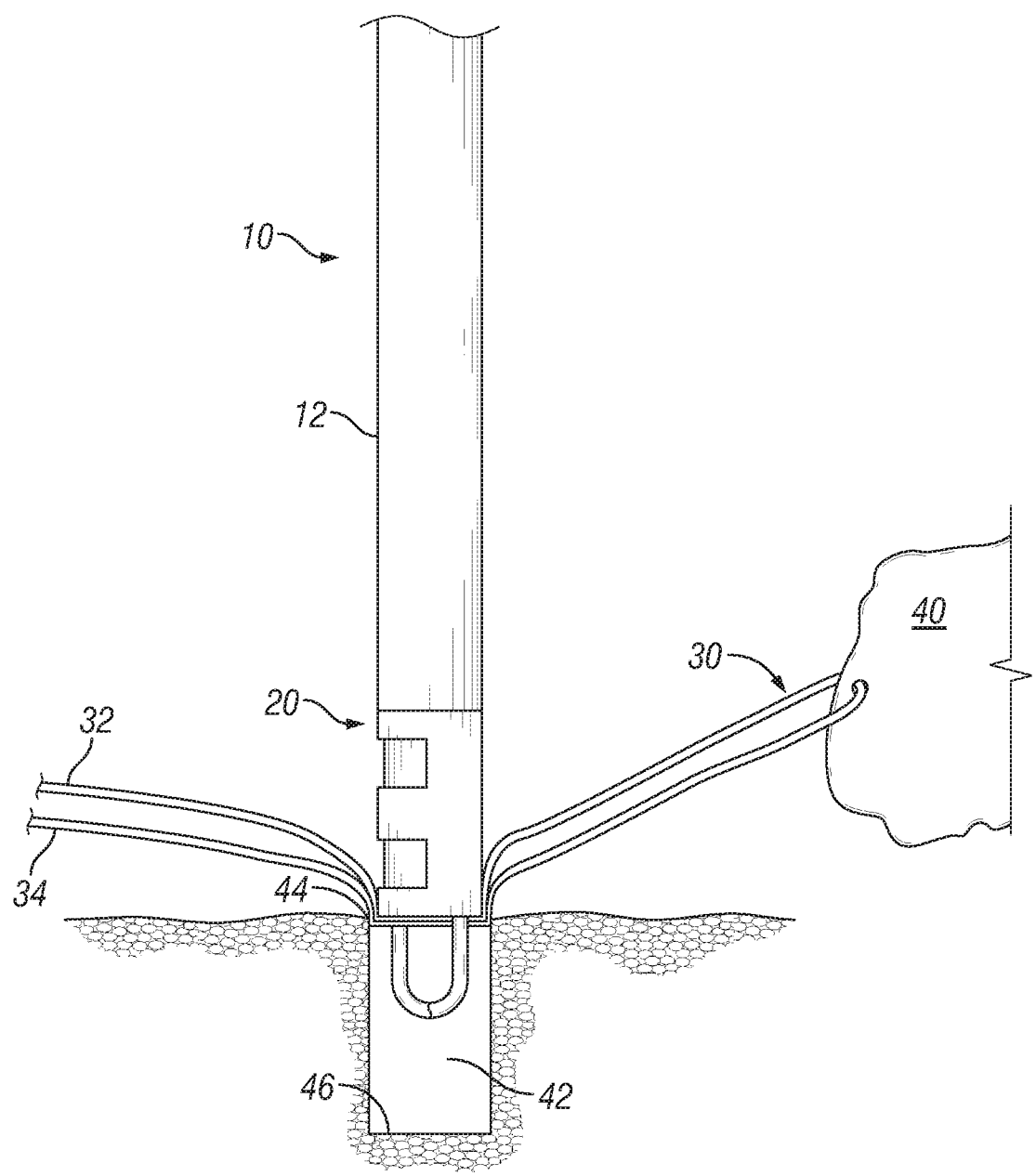
FIG. 3 illustrates another step of the method embodiment of FIG. 2.

Thereafter, the distal end of the inserter 10, with the sleeve 20 and at least a portion of the working suture 30 loaded thereto, is inserted into a bore hole 40 previously formed in bone, as best shown in FIG. 3. Slight tension is preferably applied to the free ends 32, 34 during insertion to help ensure that the working filament 30 does not become tangled or bunched within the bore hole 42. The inserter 10 is continuously pushed into bore hole 42 until the sleeve 20 is completely disposed therein and, preferably, at least a portion of the outer sheath 12 is also disposed within the bore hole 12 to ensure placement of the sleeve 20 within bone. The outer diameter of the sleeve 20 is sized with respect to the diameter of the bore hole 42 to provide a tight fit within the bore hole 42 when inserted. When fully inserted, the sleeve 20 stands upright such that the second end 24 of sleeve 20 is adjacent the base 46 of the bore hole 42 and the first end 22 of sleeve 20 is adjacent the opening 44 of the bore hole 42. As in FIG. 4, a portion of the working filament 30 may be disposed between the second end 24 of sleeve 20 and the base 46 of the bore hole 42.

Once fully inserted into the bore hole 42, the inner member 14 may be retracted within the outer sheath 12 while the outer sheath 12 remains in substantially the same position. As the inner member 14 is retracted, the outer sheath 12 prevents the sleeve 20 from being displaced from the bore hole 42 by the retraction of the inner member 14. Additionally, the friction applied to the inner surfaces of sleeve 20 by the inner member 14 may cause sleeve 20 to buckle or collapse in a longitudinal direction, which, in turn, may cause the outer surface of sleeve 20 to expand outwardly and firmly press against the inner surface of the bore hole 42. It is noted that the corresponding dimensions between the outer sheath 12 and sleeve 20 allow the distal end of the outer sheath 12 to at least partially enter into the bore hole 42 while prohibiting the sleeve 20 from being incidentally removed from the bore hole 42 as inner member 14 is retracted.

Figure 4:
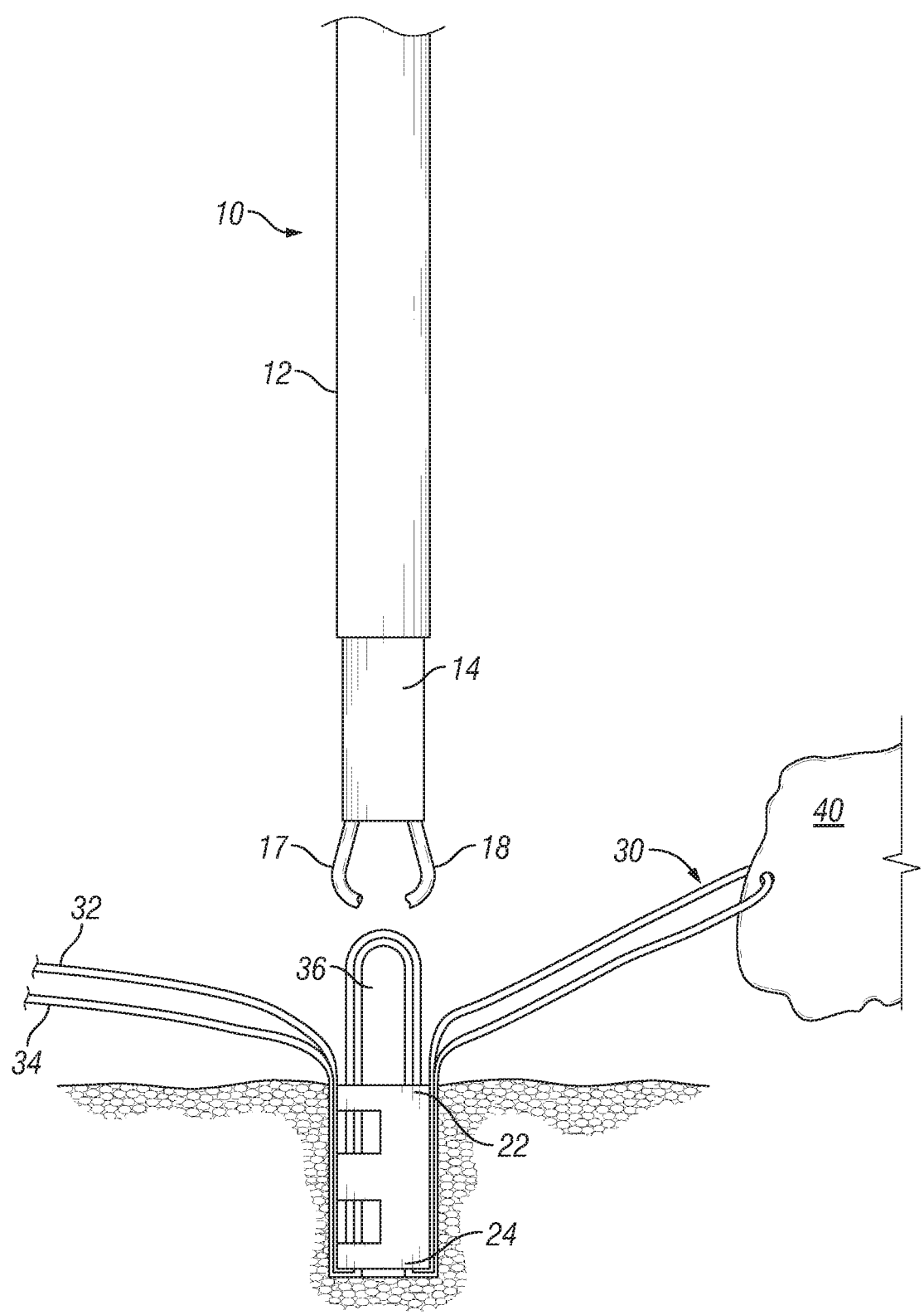
FIG. 4 illustrates an additional step of the method embodiment of FIGS. 2 and 3.

As the inner member 14 is retracted within the outer sheath 12, the actuating member 15 pulls at least a portion of the working filament 30 into and through the aperture 26 to form a first loop configuration 36 extending from the first end 22 of sleeve 20. Once, the inner member 14 is fully retracted within the outer sheath 12, the distal end of the outer sheath 12 may be removed from the bore hole 42 and the moveable arms 17, 18 actuated to the second position so that the first loop configuration 36 is released from the actuating member 15, as best seen in FIG. 4. At this point, the routing of the working filament 30 is as such: the working filament 30 extends from the tissue 40 and enters through the opening 44 of the bore hole 26; runs along the outer surface of sleeve 20 towards the base 46 of the hole 42; enters into the second end 24 of sleeve 20 adjacent the base 46 of bore hole 42; extends through the aperture and exits and then reenters the aperture 26 at the first end 22 of sleeve 20 to form the first loop configuration 36; exits the second end 22 of sleeve 20; and runs along the outer surface of sleeve 20 toward the bore hole opening 44, terminating at the first and second free ends 32, 34 exiting from the bore hole 42.

With the free ends 32, 34 extending from the bore hole 42, the free ends 32, 34 are passed through the first loop configuration 36 to form a second loop configuration 38 formed between the first and second ends 22, 24 of sleeve 20. It is noted that when the first loop configuration 36 is first formed by the inserter 10, the first loop configuration 36 may be pulled through an arthroscopic cannula where the operator releases the first loop configuration 36 from the inserter 10 for manipulation by the operator outside of the patient. Such manipulation may include forming the second loop configuration 38 with the free ends 32, 34 outside of the patient.

Figure 5:
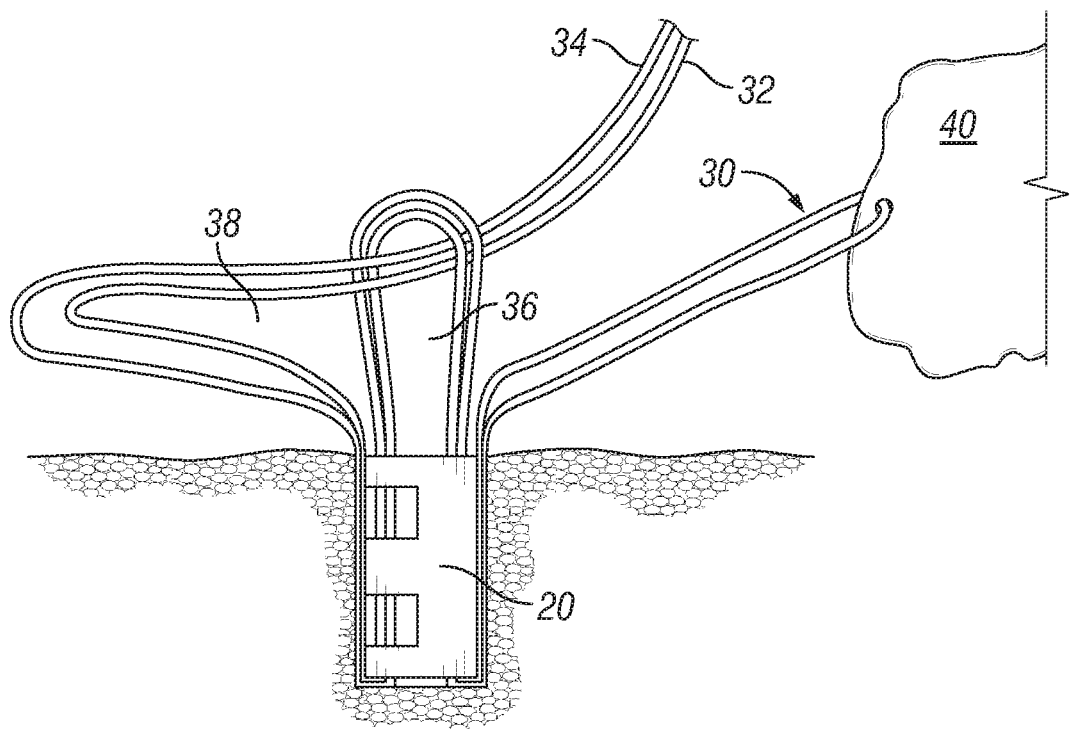
FIG. 5 illustrates a further step of the method embodiment of FIGS. 2-4.
Figure 6:
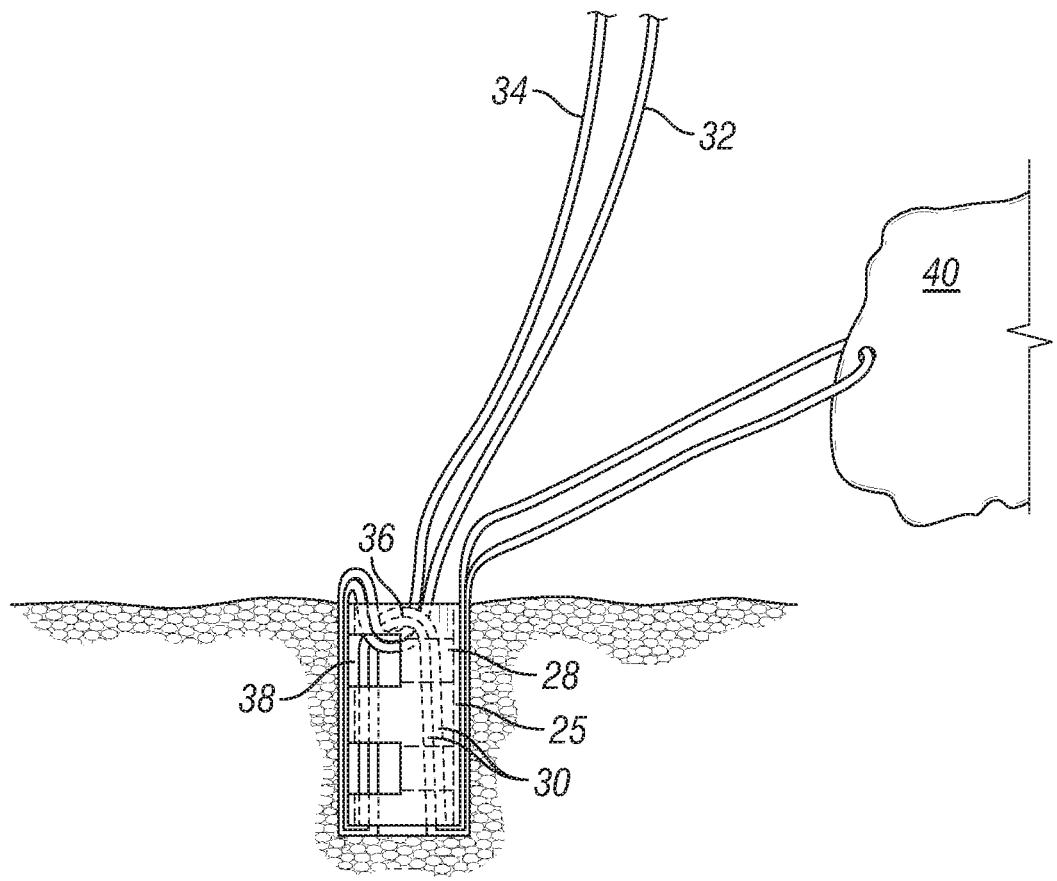
FIG. 6 illustrates yet another step of the method embodiment of FIGS. 2-5.
Figure 7:
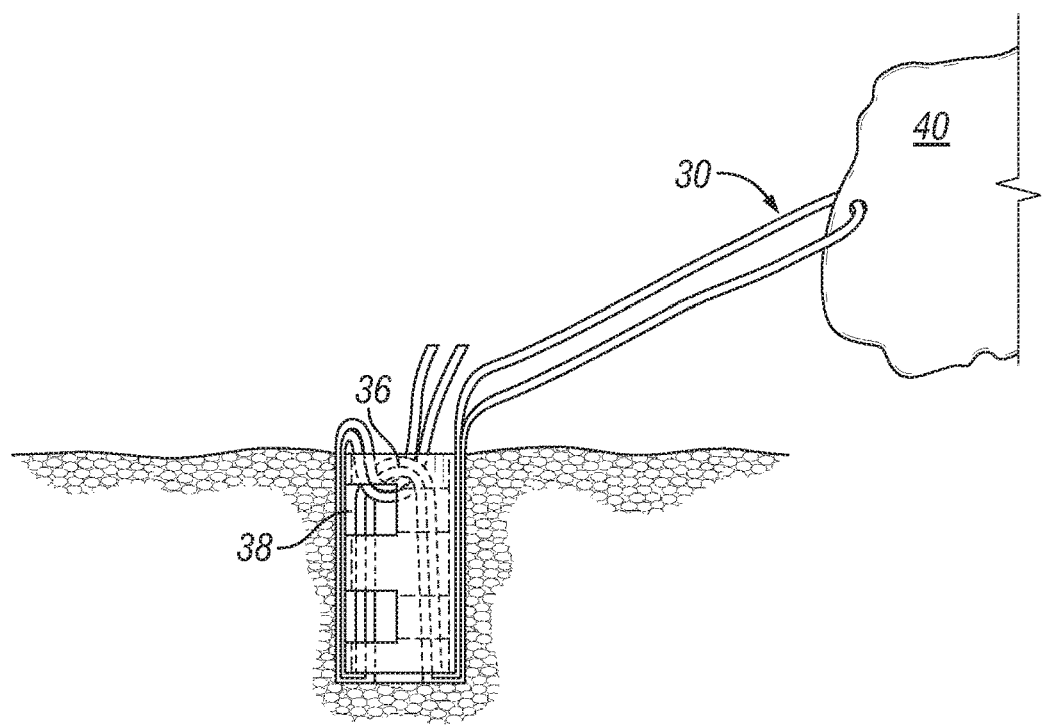
FIG. 7 illustrates a still further step of the method embodiment of FIGS. 2-6.

Once the free ends 32, 34 are passed through the first loop configuration 36, the free ends are tensioned, as shown in FIGS. 5 and 6. As tension is applied to the free ends 32, 34, the first loop configuration 36 contracts and moves towards the aperture 26 of sleeve 20 and the portion of the working filament 30 disposed between the tissue 40 and bore hole 42 tensions the tissue 40, and in some applications, draws tissue 40 closer to the bore hole 42. As tension is continuously applied to free ends 32 and 34, the first loop configuration 36 constricts the portion of the working filament 30 passing therethrough, the second loop configuration 38 cinches down and constricts sleeve 20. The friction applied to the working filament 30 and sleeve 20 caused by the constriction of these loop configurations 36, 38 creates a one-way cinch/one-way locking cleat (best shown in FIG. 6) that allows the working filament 30 to slide toward the operator through the first loop configuration 36, but prevents the slackening of the working filament 30 between the first loop configuration 36 and tissue 40 when the operator removes tension from the free ends 32, 34. Additionally, the constriction of the sleeve 20 by the second loop configuration 38 may axially compress the sleeve 20, which, in turn, helps further expand the outer surfaces of sleeve 20 against inner surface of the bore hole 42, which facilitates firm anchoring of the sleeve 20 to bone, thereby increasing pullout strength. Once the tissue 40 and one-way cinch is sufficiently tensioned, the operator may cut the free ends 32, 34, as illustrated in FIG. 7. While no knots are required to maintain this repair, the surgeon may create one or more knots utilizing the free ends of the filament, as known in the art.

Figure 8:
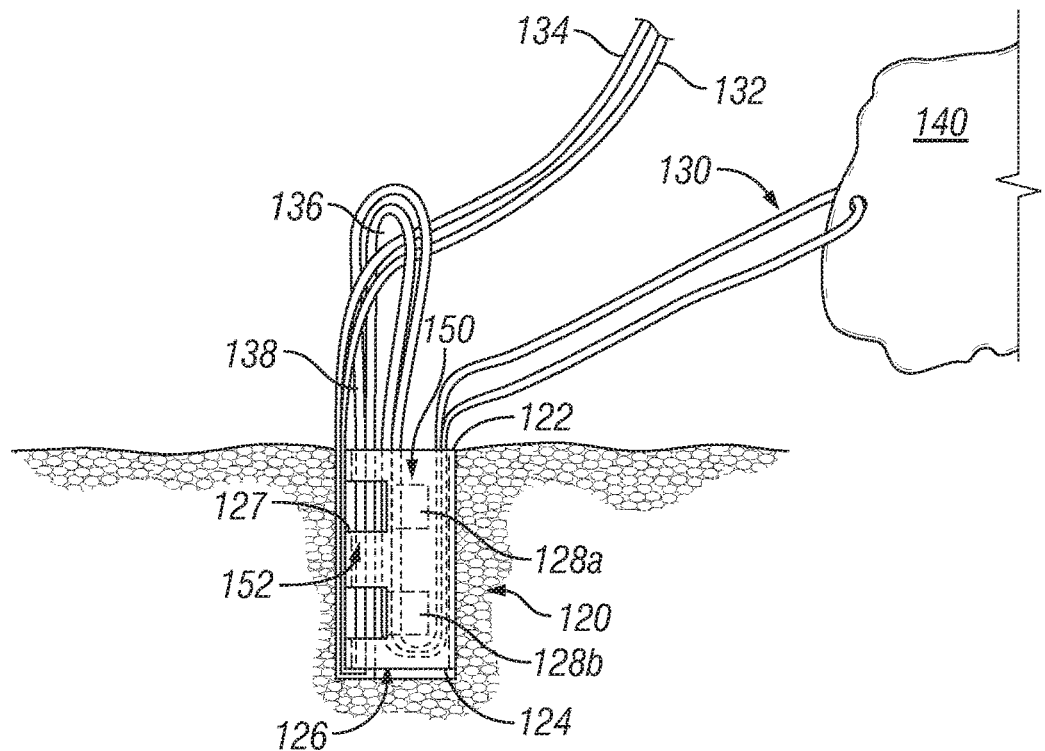
FIG. 8 illustrates an alternative method of use or assembly.

FIG. 8 depicts an alternative routing embodiment of working filament 130 with respect to anchoring sleeve 120. As discussed above, anchoring sleeve 120 is depicted as having two pairs of slits 127 forming two tabs 128a, 128b which do not invert to lie flush against the inner sidewall of the sleeve 120. Anchoring sleeve 120 can have more or less tabs than shown, and is similar to anchoring sleeve 20. Generally, with the sleeve 120 disposed within a bore hole 142 in the orientation previously described, free ends 132, 134 extend from the target tissue 140 and enter through the first end 122 of sleeve 120 into a first pathway 150 defined within the aperture by the tabs 128a, 128b and inner sidewall of sleeve 120. The free ends 132, 134 extend through the first pathway 150 in a first direction toward the second end of sleeve 120 and the base 146 of the bore hole 142. The free ends 132, 134 curve around the second tab 128b and extend through a second pathway 152 defined within aperture 126 also by the tabs 128a, 128b and inner sidewall in a second direction toward the first end 122. Free ends 132, 134 extend from and reenter the first end 122 of sleeve 120 into the second pathway 152 to form a first loop configuration 136 similar to first loop configuration 36. First and second ends 132, 134 then pass back through the second pathway 152 and extend out of the second end of sleeve 120 where the first and second free ends 132, 134 travel along the outside of sleeve 120 toward the opening of the bore hole 142 where the free ends 132, 134 exit through the bore hole 142. The free ends 132, 134 pass through the first loop configuration 136 to form a second loop configuration 138 much like second loop configuration 38.

This routing configuration is similar to the routing configuration previously described with respect to sleeve 20 but differs in that working filament 130 is first routed through the first pathway 150 within the aperture 126 rather than along the outer surface of the sleeve. Such routing is facilitated by the tabs 128a, 128b being disposed within aperture 126 to help define the first and second pathways 150, 152.

In an alternative method of use of inserter 10 and/or method of assembly of an anchoring assembly that includes sleeve 120 and working filament 130, working filament 130 is retrieved after ensnaring the target tissue 140 and passed through the first pathway 150 of sleeve 120 from the first end 122 toward the second end 124 of sleeve 120. The passage of the working filament 130 through the first pathway 150 is preferably performed during the procedure and preferably outside of the patient where the procedure is performed arthroscopically. With the free ends 132, 134 extending through the first pathway 150, the sleeve 120 is loaded onto the inner member 14, which is sized to be positioned through the second pathway 152 such that the first end 122 of sleeve 120 abuts outer sheath 12.

Once sleeve 120 is loaded onto the inner member 14 of inserter 10, the working filament 130 extending from the second end 124 of sleeve 120 is either threaded through the opening 16 between the moveable arms 17, 18 or grabbed by the actuation of the arms 17, 18 from the second to the first position. Thereafter, sleeve 120 is inserted into the bore hole 142 and the inner member 14 is retracted through the first pathway 150 in a similar fashion as previously described to form the first loop configuration 136. The working ends 132, 134 are passed through the first loop configuration 136 to form the second loop configuration 138 and one-way cinch, as shown in FIG. 8.

Figure 9:
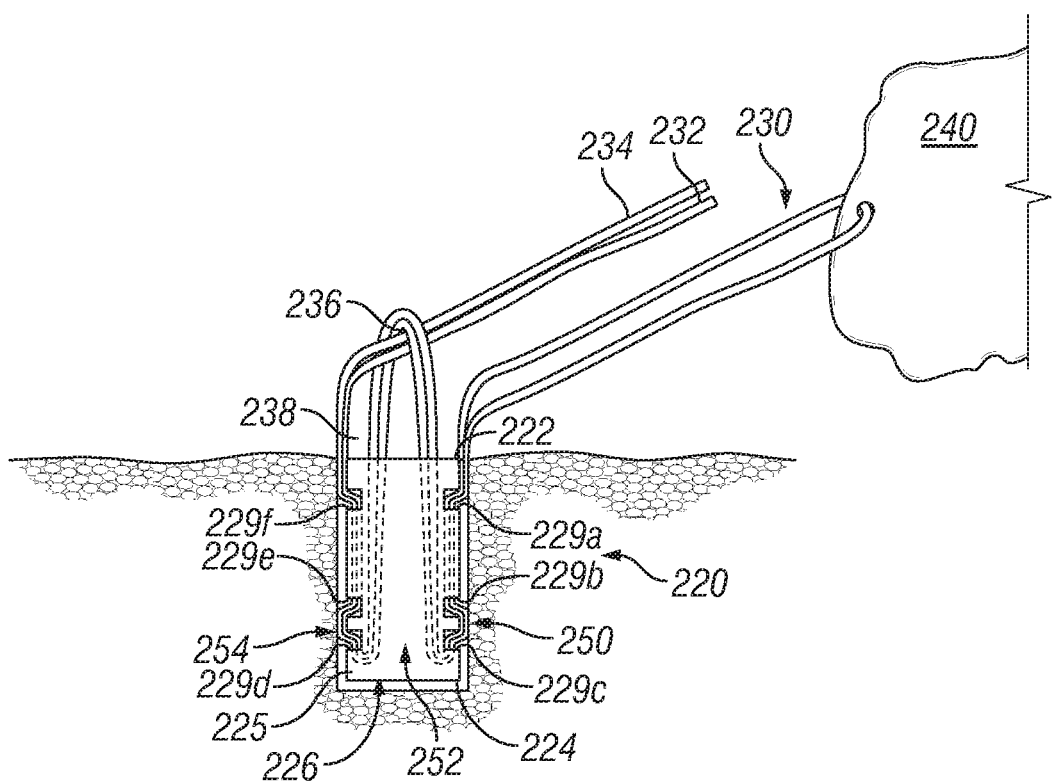
FIG. 9 illustrates another embodiment of an anchoring sleeve and an alternative method of use or assembly.

FIG. 9 depicts another of the many possible sleeve embodiments and working suture routings. Sleeve 220 includes six fenestrations 229a-f, although sleeve 220 could include more or less fenestrations. These fenestrations 229a-f extend through the sidewall 225 of sleeve 220 into an aperture 226 formed therein. Generally, a first group of three fenestrations 229a-c are aligned along the length of the sleeve 220, and another group of three fenestrations 229d-f are aligned along the length of the sleeve in an opposite location from the first group of fenestrations 229a-229c. It is noted that this is merely an example, as sleeve 220 can have a group of two or more fenestrations in various locations around the circumference of sleeve 220. It is also noted that the fenestrations 229a-f in this embodiment are not formed by the positioning of a tab within the aperture 226, rather fenestrations 229a-f may be gaps within the braiding of the sleeve 220 or holes of various shapes formed in the sidewall 225 of sleeve 220.

Generally, with sleeve 220 disposed within a bore hole 242 in bone in an upright orientation as previously described, free ends 232, 234 extend from the target tissue 240 and enter into the bore hole 242 between the sleeve's outer surface and bore hole's inner surface. Free ends 232, 234 enter the aperture 226 through the first fenestration 229a and run along the inner surface of the sleeve 220 where free ends 232, 234 pass through the second fenestration 229b and extend along the outer surface of sleeve 220. From the outer surface of sleeve 220, free ends 232, 234 extend through the third fenestration 229c where the working filament 230 forms a first loop configuration 236, similar to first loop configurations 36 and 136, such that the first loop configuration 236 extends from the first end 222 of sleeve 210. From the first loop configuration 236, free ends 232, 234 extend through the fourth fenestration 229d and run along the outer surface of sleeve 220 where the ends pass through the fifth fenestration 229e. The free ends 232, 234 extend along the inner surface of sleeve 220 and then pass through the sixth fenestration 229f where the ends run along the outer surface of sleeve 220 and out of the opening 244 of the bore hole and through the first loop configuration 236 to form a second loop configuration 238 and one-way cinch, as previously described.

The sidewall 225 between the second and third fenestrations 229b, 229c and between the fourth and fifth fenestrations 229d, 229e helps to form three separate pathways 250, 252 and 254. In some embodiments, the sidewall 225 between these fenestrations 229b-e may be narrower, that is, has a smaller diameter, than the remainder of sleeve 220. In other embodiments, the sidewall 225 between the second and third fenestrations 29b, 229c and fourth and fifth fenestrations 229d, 229e may act like tabs, such as tabs 28 and 128, formed by these fenestrations 229b-e, wherein such tabs/sidewall can be pushed or otherwise placed within the aperture 226 or merely provide boundaries forming separate routes of travel for the working filament 230.

In a method of use or method of assembly of an anchoring assembly comprised of sleeve 220 and working filament 230, working filament 230 is retrieved after ensnaring the target tissue 240. In arthroscopic procedures, the first and second ends 232, 234 of the working suture 230 may be withdrawn through an arthroplasty cannula for manipulation by the operator outside the patient. The free ends 232, 234 are then routed through the sleeve 220 by first running the free ends 232, 234 along the first pathway 250 by passing the free ends 232, 234 through the first fenestration 229a, along the inner surface of sleeve 220, through second fenestration 229b and then through the third fenestration 229c into a second pathway 252. The free ends 232, 234 are then extended across the second pathway 252 through the fourth fenestration 229*d* and into the third pathway 254. The free ends 232, 234 are extended along the third pathway 254 through the fifth and sixth apertures 229*e* and 229*f*. Generally, the working filament 230 is provided enough slack as it crosses the second pathway 252 to provide room for sleeve 220 to be loaded onto an inserter, such as inserter 10. As discussed in greater detail below, a loader, such as loader 360 in FIG. 10, can be used to route the filament 230 through the various fenestrations as illustrated. The loader may be pre-positioned through the fenestration(s) 229*a*-*f* so that the working filament 230 can be loaded into the loader loop, and with tension applied to the loader, pulled through the desired fenestration(s) 229*a*-*f*.

Thereafter, sleeve 220 may be loaded onto inserter 10 by sliding the sleeve 220 onto the inner member 14 as previously described. The actuating member 15 may then be actuated to move the arms 17 and 18 from the second to the first position to grab the working filament 230 adjacent the second end of sleeve 220. Sleeve 220 is then inserted into a bore hole 242 and the inner member 14 is retracted into the outer sheath 12, as previously described herein. While the inner member 14 is retracted, tension is applied to the working filament 230 by the actuating member 15, which may pull the third and fourth fenestrations 229*c*, 229*d* closer to the second and third fenestrations 229*b*, 229*e*, respectively. This may cause the sleeve sidewall 225 about the sleeve's circumference between the second and third fenestrations 229*b*, 229*c* and fourth and fifth fenestrations 229*d*, 229*e* to collapse and expand outwardly against the inner surface of the bore hole 242 to facilitate a firm anchoring position. In some embodiments, the sleeve sidewall 225 about the sleeve's circumference between the first and second fenestrations 229*a*, 229*b* and between the fifth and sixth fenestrations 229*e*, 229*f* may also collapse in this manner.

Once the inner member 14 is fully retracted and the first loop configuration 236 is formed, the filament free ends 232, 234 may be passed through the first loop configuration 236 to form a second loop configuration 238 and one-way cinch. Tension is applied to the filament free ends 232, 234, which locks down the one-way cinch, and may also help further collapse the sidewall segments between fenestrations 229*a*-*f* to further anchor sleeve 220 in the bore hole 242.

Shifting focus of the description, alternative inserter devices and methods of use are now described. With reference to FIGS. 1-4, in one alternative embodiment (not shown) of inserter 10, the outer sheath 12 and inner member 14 may instead be first and second portions of a monolithic structure, such that the first and second portions are rigidly fixed to each other. In such an embodiment, the outer sheath 12 would be a first portion having a first diameter, and the inner member 14 would be a second portion extending from the first portion and having a second diameter. In one embodiment, the first diameter may be larger than the second diameter such as to form a shoulder, similar to shoulder 13, at the interface between the first and second portions. The differences in these diameters may be such that when sleeve 20 is loaded onto the second portion, the outer surfaces of sleeve 20 are substantially tangent to the outer surfaces of the first portion. In another embodiment, the first and second diameters may be substantially the same.

In one embodiment of using such alternative monolithic inserter device, sleeve 20 may be loaded onto the second portion such that sleeve 20 abuts the shoulder. A working filament, such as working filament 30, may be grasped by the inserter, and then the inserter and sleeve 20 may be inserted into a bore hole in bone, as previously described with regard to inserter 10. However, unlike with inserter 10, the monolithic inserter may simply be pulled out of the bore hole once sleeve 20 is fully inserted into the bore hole. The second portion of inserter may have a highly polished outer surface such that the friction applied by the inner surface of the bore hole against the outer surface of the sleeve 20 is greater than the friction applied to the inner surface of the sleeve 20 as the inserter 10 is removed, which may facilitate the bunching effect as previously described, and also allow the monolithic inserter to be removed without incidental removal of sleeve 20 from the bore hole.

Figure 10:
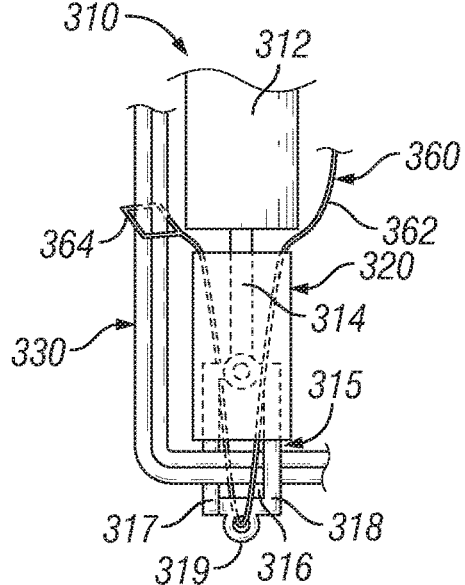
FIGS. 10-12 illustrate another embodiment of an inserter device and method of use or assembly.
Figure 11:
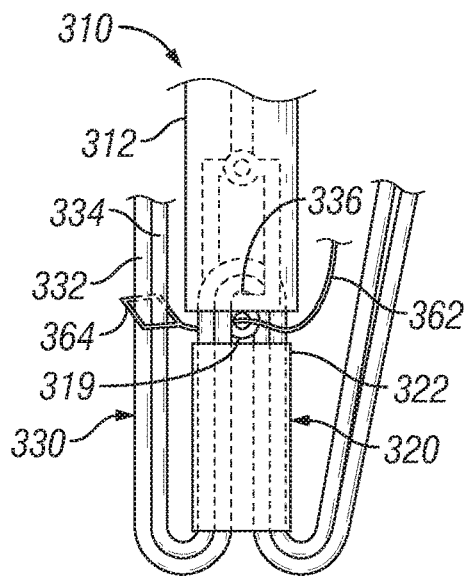
Figure 12:
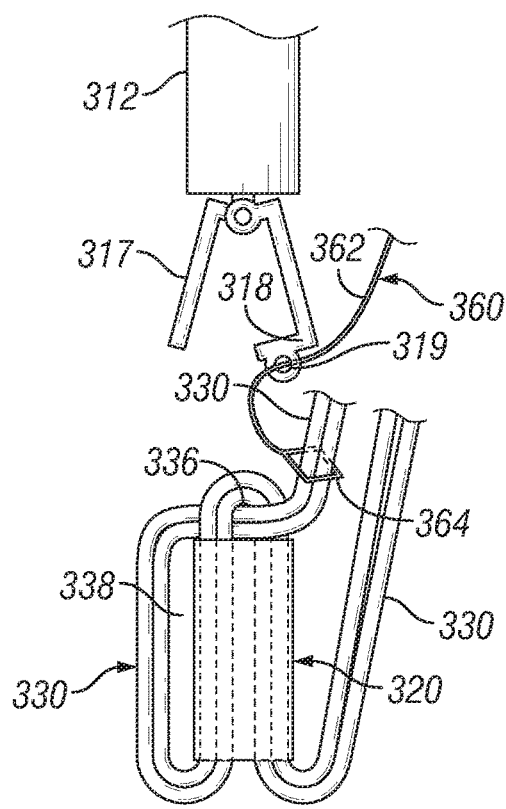

FIGS. 10-12 depict another alternative embodiment of an inserter and method of use and/or method of assembly of an anchoring assembly comprised of sleeve 320 and working filament 330. Similar to inserter 10, inserter 310 includes an outer sheath 312 and inner member 314. The inner member 314 also includes an actuation member 315 that includes first and second arms 317, 318 that are clampable together at their respective distal ends to form an opening 316 for retaining the working filament 330. However, unlike inserter 10, inserter 310 includes an eyelet 319 extending distally from the first or second arm member 317, 318 and a loader 360 that can be passed through the eyelet 319.

The loader 360 may be a thread formed from filamentary material or wire formed from memory metal material, such as a nickel-titanium alloy, also known as Nitinol, or the like. The loader 360 may have an elongate tail 362 and looped head 364 disposed at the end of the elongate tail 362. The looped head 364 may have a diamond, ovular, or circular shape, for example. An example of a Nitinol loader is disclosed in U.S. application Ser. No. 14/104,480, filed on Dec. 12, 2013, the entirety of which is hereby incorporated by reference herein as if fully set forth herein.

In another embodiment of a method of use/assembly, the tail end of the loader 360 is passed into the eyelet 319 such that the tail 362 end extends from one side of the eyelet 319 and the head 364 end extends from the other side of the eyelet 319. Sleeve 320 is then slid over the inner member 314 and over loader 360 such that the head 364 end and tail 362 end extend from the first end 322 of sleeve 320 (best shown in FIG. 10). It is noted that in an arthroscopic procedure, the elongate tail 360 may have sufficient length to be manipulated by an operator outside of the patient through a cannula while the inserter 310 is in use in vivo. Just as with inserter 10, loading of sleeve 320 with inserter 310 can be performed during the manufacturing process and delivered to the operating room in a preloaded configuration or loaded in the operating room during or just prior to the procedure.

A working filament 330 that is coupled to the target tissue (not shown) may have a first and second free ends 332, 334 that may be passed through the opening 316 of the actuating member 315 and between the head end and tail end of the loader. The free ends 332, 334 of the working filament 330 may then be passed through the looped head 364, as shown in FIG. 10, which may be performed outside of the patient.

Thereafter, the distal end of inserter 310, with loader 360, sleeve 320, and working filament 330 engaged thereto, is inserted into a bore hole (not shown) formed in bone. Once the sleeve 320 is fully inserted into the bore hole 320, a first loop configuration 336 is formed in substantially the same manner as previously described with relation to inserter 10 by retracting the inner member 314 into the outer sheath 312. However, unlike the first loop configuration 336 formed by inserter 10, the elongate tail 362 of the loader 360 is positioned through the first loop configuration 336 once the first loop configuration 336 is formed.

With the actuating member 315 still in the first position with the first and second arm members 317, 318 clamped together, the loader 360 is tensioned such that the looped head 364 is drawn into the eyelet 319. In some embodiments, the eyelet 319 may be large enough to allow the free ends 332, 334 to pass into the eyelet 319. In other embodiments, the eyelet 319 may be small enough to prohibit the free ends 332, 334 from entering therein. In either embodiment, once the looped head 364 reaches the eyelet 319, the actuating member 315 may be actuated such that the arms 317, 318 separate. Generally the eyelet 319 is positioned on the arm 317 or 318 disposed on the opposite side of the first loop configuration 336 as the free ends 332, 334. When the arms 317, 318 separate the arm containing the eyelet 319 and looped head 364 begins to pull the free ends 332, 334 through the first loop configuration 336. The inserter 310 may then be pulled away from the bore hole which further pulls the free ends 332, 334 through the first loop configuration 336. The inserter 310 is continued to be pulled until the entirety of the free ends 332, 334 is passed through the first loop configuration 336 to form the second loop configuration 338, as depicted in FIG. 12.

Thereafter, the free ends 332, 334 may be tensioned to form the one-way cinch substantially in the same way as in the method utilizing inserter 20. Inserter device 320 allows for the formation of the one-way cinch near the bore hole, even during arthroscopic procedures, which may facilitate the use of a relatively short working filament as compared to working filament 30 utilized with inserter 10.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A suture anchor insertion assembly, comprising:
an inserter having a proximal end, a distal end, and a length extending therebetween, the distal end having an aperture surrounded by a perimeter of the aperture, the perimeter of the aperture including a first portion and a second portion of the inserter, the first and second portions being separable from each other such that in a second configuration, a distance between the first and second portions is further than in a first configuration so that a gap is formed between the first and second portions in the second configuration allowing a filament captured within the aperture to be released from the aperture through the gap; and
a bone anchor having a length extending between first and a second ends thereof and an opening extending along the length, the bone anchor being a filamentary sleeve and disposed over a portion of the length of the inserter such that the distal end of the inserter extends from a first end of the bone anchor.

2. The assembly of claim 1, wherein the first and second portions are curved towards each other such that, in the first position, respective distal ends of the first and second portions face each other.

3. The assembly of claim 2, wherein, in the second position, the distal ends of the first and second portions are positioned further apart from each other than in the first position such that the gap is formed between the distal ends.

4. The assembly of claim 1, wherein the inserter includes an elongate shaft and the bone anchor is positioned over the elongate shaft such that the elongate shaft extends through the opening of the bone anchor.

5. The assembly of claim 4, wherein the first and second portions extend from an end of the elongate shaft.

6. The assembly of claim 1, wherein the first and second portions are adapted to pass through the opening of the bone anchor.

7. A suture anchor insertion assembly comprising:
an inserter having a proximal end, a distal end, and a length extending therebetween, the distal end having first and second members extending therefrom, the first and second members defining a perimeter of an aperture that extends between the first and second members, the first and second members having a first configuration in which the first and second members form a closed perimeter about the aperture so as to capture a filament within the perimeter, and a second configuration in which the first and second members form an open perimeter about the aperture so as to allow the filament to escape through a gap formed in the open perimeter; and
a bone anchor being a filamentary sleeve and having a length extending between first and a second ends thereof and an opening extending along the length of the bone anchor, the inserter extending through the opening of the bone anchor so that the first and second members are positioned closer to the first end of the bone anchor than the second end thereof.

8. The assembly of claim 7, wherein, in the first configuration, the first and second members are continuous with each other, and in the second configuration, the first and second members are discontinuous with each other via the gap.

9. The assembly of claim 7, wherein, in the first configuration, distal ends of the first and second members contact each other, and in the second configuration, the distal ends of the first and second members do not contact each other.

10. The assembly of claim 7, wherein the inserter includes an elongate shaft and the bone anchor is positioned over the elongate shaft such that the elongate shaft extends through the opening of the bone anchor.

11. The assembly of claim 10, wherein the first and second members extend from an end of the elongate shaft.

12. The assembly of claim 7, wherein the first and second members are adapted to pass through the opening of the bone anchor.

13. A method of anchoring soft tissue to bone comprising:
capturing a length of filament connected to soft tissue with a distal end of an inserter such that the length of filament extends through an aperture defined by the inserter;
inserting the distal end of the inserter into a bone hole in a bone such that the aperture and a bone anchor positioned over a portion of a length of the inserter are positioned within the bone hole;
releasing the filament through a gap formed in the distal end of the inserter adjacent to the aperture; and
drawing the distal end of the inserter through the bone anchor from a first end to a second end thereof while the bone anchor remains positioned within the bone hole, the drawing step being performed before the releasing step so that a portion of the length of filament is positioned in the opening of the bone anchor.

14. The method of claim 13, wherein the drawings step includes moving an inner member relative to an outer sheath positioned over the inner member, the bone anchor being positioned over the inner member.

15. The method of claim 13, wherein the perimeter of the aperture includes a first portion of the perimeter and a second portion of the perimeter, wherein the gap is formed by the first and second portions of the aperture separating from one another.

16. The method of claim 13, forming the gap between first and second members of the distal end of the inserter, the first and second members defining a perimeter of the aperture.

\* \* \* \* \*